(12) United States Patent
Leonard

(10) Patent No.: US 12,702,771 B2
(45) **Date of Patent: *Aug. 11, 2026**

(54) INTERNAL CANNULA MOUNTED NEBULIZER

(71) Applicant: Vapotherm, Inc., Exeter, NH (US)

(72) Inventor: Scott A. Leonard, Bedford, NH (US)

(73) Assignee: VAPOTHERM, INC., Exeter, NH (US)

( * ) Notice: Subject to any disclaimer, the term of this patent is extended or adjusted under 35 U.S.C. 154(b) by 88 days.

This patent is subject to a terminal disclaimer.

(21) Appl. No.: 18/532,442

(22) Filed: Dec. 7, 2023

(65) Prior Publication Data

US 2024/0358939 A1 Oct. 31, 2024

Related U.S. Application Data

(63) Continuation of application No. 17/032,751, filed on Sep. 25, 2020, now Pat. No. 11,878,115.

(Continued)

(51) Int. Cl.

*A61M 15/00* (2006.01)
*A61M 15/08* (2006.01)
*A61M 16/06* (2006.01)

(52) U.S. Cl.

CPC ........ *A61M 15/08* (2013.01); *A61M 15/0085* (2013.01); *A61M 16/0666* (2013.01); *A61M 2205/50* (2013.01); *A61M 2206/20* (2013.01)

(58) Field of Classification Search

CPC .............. A61M 15/08; A61M 15/0085; A61M 16/0666; A61M 2205/05; A61M 2206/20

See application file for complete search history.

(56) References Cited

U.S. PATENT DOCUMENTS 1,149,010 A 8/1915 Olive
2,485,184 A 10/1949 Blackman et al.

(Continued)

FOREIGN PATENT DOCUMENTS

DE 202013006445 8/2013
EP 1317941 6/2003

(Continued)

OTHER PUBLICATIONS

Cairo, "Mosby's Respiratory Care Equipment," 9th Ed. pp. 20, 98 (2014) (4 pages).

(Continued)

*Primary Examiner* — Margaret M Luarca
*Assistant Examiner* — Sarah B Lederer
(74) *Attorney, Agent, or Firm* — McDermott Will & Schulte LLP

(57) ABSTRACT

Provided herein are devices, systems, and methods for providing respiratory therapy to a patient using a nasal cannula comprising a cannula body, first and second inlet tubes, and a nasal prong for the delivery of a flow of breathing gas to the patient. Configured with the cannula is a nebulizer having an aerosol generator positioned to emit aerosolized medicament along a longitudinal axis of the nasal prong. A flow director is configured to direct the flow of breathing gas into the nasal prong such that the breathing gas flows along the longitudinal axis, such that the flow of aerosolized medicament is contained within the flow of breathing gas as it moves along the longitudinal axis of the nasal prong for delivery to the patient.

33 Claims, 9 Drawing Sheets

Related U.S. Application Data

(60) Provisional application No. 62/906,404, filed on Sep. 26, 2019.

(56) References Cited

U.S. PATENT DOCUMENTS

RE24,534 E 9/1958 Dahl
2,941,544 A 6/1960 Peras
3,826,255 A 7/1974 Havstad
3,864,326 A 2/1975 Babington
3,945,378 A 3/1976 Paluch
4,003,398 A 1/1977 Duveau
4,028,072 A 6/1977 Braun
4,177,945 A 12/1979 Schwartz et al.
4,270,564 A 6/1981 Blackburn
4,422,456 A 12/1983 Tiep
4,708,166 A 11/1987 Kobold
4,782,832 A 11/1988 Trimble
4,790,308 A 12/1988 Weichselbuam
4,805,609 A 2/1989 Roberts et al.
4,819,625 A 4/1989 Howe
4,832,012 A 5/1989 Raabe et al.
4,911,157 A 3/1990 Miller
4,915,105 A 4/1990 Lee
4,951,661 A 8/1990 Sladek
5,099,833 A 3/1992 Michaels
5,099,836 A 3/1992 Rowland
5,113,911 A 5/1992 Hirsh
5,226,411 A 7/1993 Levine
5,335,656 A 8/1994 Bowe et al.
5,433,242 A 7/1995 Buchtel
5,461,695 A 10/1995 Knoch
5,584,285 A 12/1996 Salter et al.
5,630,409 A 5/1997 Bono et al.
5,645,539 A 7/1997 Solomon
5,752,511 A 5/1998 Simmons
6,017,315 A 1/2000 Starr
6,315,739 B1 11/2001 Merilainen
6,328,030 B1 12/2001 Kidwell et al.
6,530,370 B1 3/2003 Heinonen
6,539,937 B1 4/2003 Haveri
6,561,188 B1 5/2003 Ellis
6,769,626 B1 8/2004 Haveri
6,805,126 B2 10/2004 Dutkiewicz
6,986,353 B2 1/2006 Wright
7,007,694 B2 3/2006 Acoba
7,481,244 B2 1/2009 Bivin
7,662,181 B2 2/2010 Deem
7,743,770 B2 6/2010 Curti
7,832,400 B2 11/2010 Labs
8,561,607 B2 10/2013 Cortez, Jr. et al.
8,631,799 B2 1/2014 Davenport
8,740,808 B2 6/2014 Curti
9,333,317 B2 5/2016 Cortez, Jr. et al.
9,597,263 B2 3/2017 Visveshwara
9,822,515 B2 11/2017 Wu
9,925,348 B2 3/2018 Payton et al.
10,100,622 B2 10/2018 Gonzalez
10,265,494 B2 4/2019 Cortez, Jr. et al.
10,300,236 B2 5/2019 Cortez, Jr. et al.
10,471,227 B1 11/2019 Morris
11,420,002 B2 8/2022 Evans et al.
11,878,115 B2* 1/2024 Leonard ............ A61M 16/0666
2002/0053346 A1 5/2002 Curti et al.
2003/0150445 A1 8/2003 Power et al.
2004/0011364 A1 1/2004 Dhuper et al.
2004/0112383 A1 6/2004 Curti
2004/0221846 A1 11/2004 Curti et al.
2004/0226566 A1 11/2004 Gunaratnam et al.
2004/0237178 A1 12/2004 Landeros
2005/0005942 A1 1/2005 Aylsworth
2005/0028822 A1 2/2005 Sleeper et al.
2005/0066976 A1 3/2005 Wondka
2005/0103347 A1 5/2005 Curti et al.
2005/0121033 A1 6/2005 Starr
2005/0217667 A1 10/2005 Dhuper et al.
2005/0229926 A1 10/2005 Fink et al.
2005/0229927 A1 10/2005 Fink et al.
2005/0229928 A1 10/2005 Ivri et al.
2005/0229929 A1 10/2005 Ivri et al.
2005/0252509 A1 11/2005 Rustad
2006/0078506 A1 4/2006 Niven et al.
2006/0120938 A1 6/2006 Kanno
2006/0120968 A1* 6/2006 Niven .................. A61M 16/14 128/200.23
2006/0230929 A1 10/2006 Bliss
2006/0230931 A1 10/2006 Bliss
2007/0107731 A1 5/2007 Landis
2007/0175473 A1 8/2007 Lewis et al.
2008/0000470 A1 1/2008 Minocchieri et al.
2008/0121230 A1 5/2008 Cortez et al.
2008/0223375 A1 9/2008 Cortez et al.
2009/0044808 A1 2/2009 Guney
2009/0101147 A1 4/2009 Landis
2009/0241948 A1 10/2009 Clancy et al.
2009/0250132 A1 10/2009 Bivin
2009/0253995 A1 10/2009 Lewis et al.
2010/0089395 A1 4/2010 Power et al.
2010/0096019 A1 4/2010 DiPerna
2010/0108073 A1 5/2010 Zollinger et al.
2010/0113955 A1 5/2010 Colman
2010/0252037 A1 10/2010 Wondka
2010/0258114 A1 10/2010 Cortez, Jr. et al.
2010/0282247 A1 11/2010 Kadrichu
2011/0000487 A1 1/2011 Moa et al.
2011/0067704 A1 3/2011 Kooij et al.
2011/0073116 A1 3/2011 Genger et al.
2011/0094518 A1 4/2011 Cipollone
2011/0146685 A1* 6/2011 Allan ................ A61M 16/0616 128/206.26
2011/0232649 A1 9/2011 Collazo et al.
2011/0271962 A1 11/2011 White et al.
2011/0284001 A1 11/2011 Tero
2012/0090622 A1 4/2012 Chang
2012/0111970 A1* 5/2012 Hogan .................. B05B 17/063 239/102.2
2012/0125332 A1 5/2012 Niland
2012/0167878 A1 7/2012 Belson et al.
2012/0304992 A1 12/2012 Ratto
2012/0325206 A1 12/2012 Allum
2013/0000641 A1 1/2013 Mazela et al.
2013/0008447 A1 1/2013 Gunaratnam et al.
2013/0074842 A1 3/2013 Boucher
2013/0092165 A1 4/2013 Wondka
2013/0152925 A1 6/2013 Rahmel et al.
2013/0160772 A1 6/2013 Tabrizchi
2013/0186395 A1 7/2013 Cortez, Jr. et al.
2013/0255670 A1 10/2013 Ott et al.
2013/0267864 A1 10/2013 Addington
2014/0066801 A1 3/2014 Tero
2014/0109899 A1 4/2014 Boucher
2014/0116447 A1 5/2014 Cortez, Jr. et al.
2014/0137744 A1 5/2014 Wilkinson
2014/0147506 A1 5/2014 Longest et al.
2014/0150789 A1 6/2014 Flanagan et al.
2014/0158127 A1 6/2014 Boucher et al.
2014/0166009 A1 6/2014 Flanagan et al.
2014/0230942 A1 8/2014 Takai
2014/0261704 A1 9/2014 Hoogenakker
2014/0366885 A1 12/2014 Haibach et al.
2015/0000654 A1* 1/2015 Martin .................. A61M 16/12 128/203.12
2015/0000659 A1 1/2015 Martin
2015/0000660 A1 1/2015 Martin
2015/0090255 A1 4/2015 Gulliver
2015/0150803 A1 6/2015 Boucher
2015/0230731 A1 8/2015 Levitsky
2015/0352299 A1 12/2015 Cortez et al.
2016/0015296 A1 1/2016 Garaycochea
2016/0015921 A1 1/2016 Harrison et al.
2016/0030696 A1 2/2016 Klenner
2016/0158476 A1 6/2016 Tatkov
2016/0271353 A1 9/2016 Cheung
2017/0000965 A1* 1/2017 Cortez, Jr. ........ A61M 16/0666
2018/0064898 A1 3/2018 Evans et al.

(56) References Cited

U.S. PATENT DOCUMENTS

| | | | | |
|---|---|---|---|---|
| 2018/0272079 | A1* | 9/2018 | Porter | A61M 16/0488 |
| 2018/0272080 | A1 | 9/2018 | Porter et al. | |
| 2019/0038851 | A1 | 2/2019 | Hijlkema | |
| 2019/0134336 | A1 | 5/2019 | Hobson | |
| 2019/0328990 | A1 | 10/2019 | Cortez et al. | |
| 2019/0328993 | A1 | 10/2019 | Cortez et al. | |
| 2019/0366016 | A1 | 12/2019 | Leonard et al. | |
| 2020/0368483 | A1 | 11/2020 | Duffy et al. | |

FOREIGN PATENT DOCUMENTS

| | | | | |
|---|---|---|---|---|
| EP | 2022528 | | 2/2009 | |
| EP | 2247331 | | 11/2010 | |
| EP | 3646913 | | 5/2020 | |
| FR | 2827778 | A1 | 1/2003 | |
| JP | 2007537833 | | 12/2007 | |
| JP | 2018089139 | | 5/2018 | |
| RU | 2009111135 | | 10/2010 | |
| RU | 2432190 | | 10/2011 | |
| WO | WO-1989009565 | | 10/1989 | |
| WO | WO-9818513 | | 5/1998 | |
| WO | WO-1998018513 | | 5/1998 | |
| WO | WO-2002004054 | | 1/2002 | |
| WO | WO-2002074372 | | 9/2002 | |
| WO | WO-2003035141 | | 5/2003 | |
| WO | WO-03050497 | | 6/2003 | |
| WO | WO-2005115520 | | 12/2005 | |
| WO | WO-2006026237 | | 3/2006 | |
| WO | WO-2006102345 | | 9/2006 | |
| WO | WO-2006138579 | | 12/2006 | |
| WO | WO-2008060587 | | 5/2008 | |
| WO | WO-2008094219 | | 8/2008 | |
| WO | WO-2009013501 | | 1/2009 | |
| WO | WO-2009078805 | | 6/2009 | |
| WO | WO-2009094532 | | 7/2009 | |
| WO | WO-2009149336 | | 12/2009 | |
| WO | WO-2010035251 | | 4/2010 | |
| WO | WO-2010091259 | | 8/2010 | |
| WO | WO-2012020004 | | 2/2012 | |
| WO | WO-2012045051 | | 4/2012 | |
| WO | WO-2013041996 | | 3/2013 | |
| WO | WO-2013042004 | | 3/2013 | |
| WO | WO-2013112545 | | 8/2013 | |
| WO | WO-2013157960 | | 10/2013 | |
| WO | WO-2013158967 | | 10/2013 | |
| WO | WO-2014070833 | | 5/2014 | |
| WO | WO-2014142681 | | 9/2014 | |
| WO | WO-2015121815 | | 8/2015 | |
| WO | WO-2015164921 | | 11/2015 | |
| WO | WO-2015188179 | | 12/2015 | |
| WO | WO-2016043607 | | 3/2016 | |
| WO | WO-2016157103 | | 10/2016 | |
| WO | WO-2016157103 | A1 * | 10/2016 | A61B 1/2733 |
| WO | WO-2017062677 | | 4/2017 | |
| WO | WO-2017127420 | | 7/2017 | |
| WO | WO-2018005851 | | 1/2018 | |
| WO | WO-2018065588 | | 4/2018 | |
| WO | WO-2018068085 | | 4/2018 | |
| WO | WO-2018172561 | | 9/2018 | |
| WO | WO-2018172562 | | 9/2018 | |
| WO | WO-2018172563 | | 9/2018 | |
| WO | WO-2019115771 | | 6/2019 | |
| WO | WO-2019115802 | | 6/2019 | |
| WO | WO-2019191814 | | 10/2019 | |

OTHER PUBLICATIONS

Doshi et al., "High-Velocity Nasal Insufflation in the Treatment of Respiratory Failure: A Randomized Clinical Trial", Annals of Emergency Medicine, Jul. 2017;72(1):73-83.

International Search Report and Written Opinion for PCT/US2010/023331 dated Oct. 19, 2010 (7 pages).

International Search Report and Written Opinion for PCT/US2013/022692 dated May 23, 2013 (18 pages).

International Search Report and Written Opinion for PCT/US2015/034663 dated Aug. 20, 2015 (7 pages).

International Search Report and Written Opinion for PCT/US2016/040465 dated Oct. 4, 2016 (16 pages).

International Search Report and Written Opinion for PCT/US2017/040079 dated Oct. 18, 2017 (21 pages).

International Search Report and Written Opinion for PCT/US2018/049979 dated Dec. 3, 2018 (16 pages).

International Search Report and Written Opinion for PCT/US2019/034978 dated Dec. 11, 2019 (24 pages).

International Search Report and Written Opinion for PCT/US2019/035008 dated Sep. 9, 2019 (17 pages).

International Search Report and Written Opinion for PCT/US2020/039641 dated Oct. 7, 2020 (13 pages).

International Search Report and Written Opinion for PCT/US2020/052808 dated Jan. 11, 2021 (9 pages).

International Search Report and Written Opinion for PCT/US2021/051987 dated Jan. 5, 2022 (19 pages).

International Search Report and Written Opinion for PCT/US2021/065088 dated Jun. 14, 2022 (27 pages).

Kacmarek et al, "Egan's Fundamentals of Respiratory Care," Physical Principles of Respiratory Care, Chap. 6, 11th Ed., pp. 123-124 (2017) (5 pages).

Sacci, R., "Air entrainment masks: Jet mixing is how they work; The Bernoulli and Venturi Principles are How They Don't", Respiratory Care 1979, vol. 24, No. 10 (4 pages).

Spence, et al, ""Development of a High-Flow Nasal Cannula and Pharmaceutical Aerosol Combination Device"", J Aerosol Med Pulm Drug Deliv. Mar. 21, 2019. doi: 10.1089/jamp.2018.1488. [Epub ahead of print] PMID: 30855199 (18 pgs).

Spivey S., et al., "Assessment of High Flow Nasal Cannula Therapy use in the Emergency Department Setting: Observations of Practice Across Four Systems", Respiratory Therapy, vol. 10, No. 1, pp. 30-34 (2015).

Supplementary European Search Report for EP13740914.0 dated Jul. 8, 2015 (2 pg).

* cited by examiner

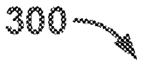
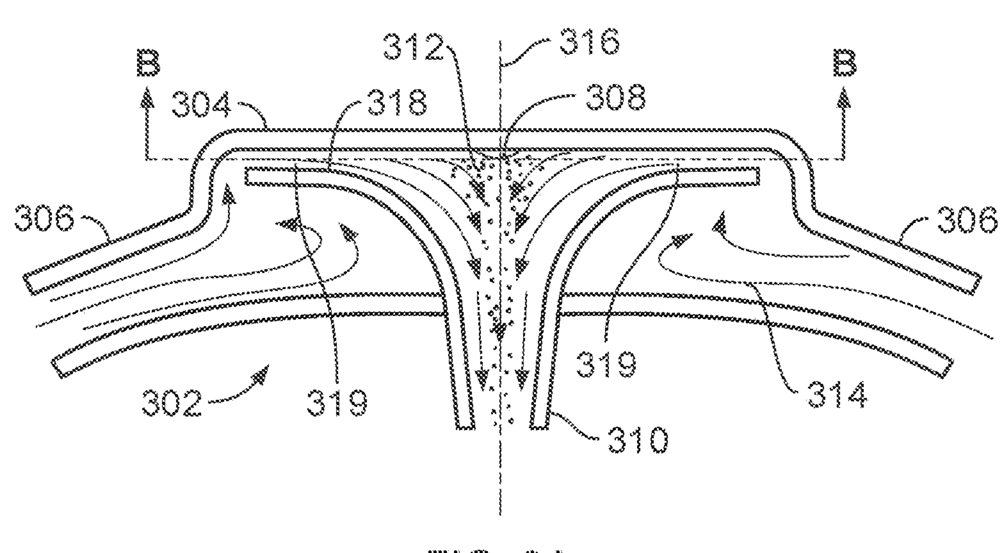
FIG. 3A
312
308
314
304
FIG. 3B

INTERNAL CANNULA MOUNTED NEBULIZER

CROSS-REFERENCE TO RELATED APPLICATIONS

This application is a continuation of U.S. Pat. No. 17,032,751, filed on Sep. 25, 2020 (U.S. Pat. No. 11,878,115), which claims priority to and the benefit of U.S. Provisional Patent Application No. 62/906,404, filed on Sep. 26, 2019, and entitled "INTERNAL CANNULA MOUNTED NEBULIZER", each of which is incorporated herein by reference in its entirety.

BACKGROUND

Patients receiving respiratory therapy by the delivery of breathing gas to the patient's nares can in some circumstances benefit from the administration of various other drug therapies. Drug therapy may be administered to a patient receiving respiratory therapy by nebulizing the drug and combining the nebulized drug with a gas flow of the respiratory therapy. A significant problem with delivering nebulized drug therapy in a respiratory therapy is rain-out which occurs when the nebulized particles impact upon a surface and stick to it (or collide and stick to each other). These stuck particles coalesce into larger droplets which are too large for respiration. Large droplets that are transmitted to the patient and enter the patient's nasal passage or airway may be clinically ineffective and irritating to the patient. Rainout can also occur when nebulized particles are contained in a flow, and that flow changes direction or encounters turbulence. Changes in flow direction or turbulence can cause particles to impact a surface and coalesce. Such is a common occurrence in conventional respiratory therapy delivery systems that involve a number of direction changes incorporated in their flow configurations.

Traditionally, nebulizers are separate devices from the gas delivery device used for respiratory therapy. As a separate device they commonly rely on an adapter to combine the nebulized drug particles with the main flow of gas from the gas delivery device. This is typically accomplished using a mixing chamber where the nebulized drug particles mix with the gas flow. Such traditional implementations of nebulizers are described in U.S. Pat. Nos. 5,645,620, 6,599,348. U.S. Patent Publication No. 2005/0229927. U.S. Patent Publication 2007/0157931, U.S. Patent Publication No. 2017/0000965, U.S. Patent Publication No. 2017/0021125, and U.S. Patent Publication No. 2017/0312472, each of which is hereby incorporated by reference in its entirety.

In particular, U.S. Patent Publication No. 2005/0229927 locates the mixing chamber very close to the cannula. This prior art configuration is shown in FIG. 1, depicting a device 100 including a mixing chamber 104 where nebulizer particles 112 from emitter 108 are mixed with breathing gas 114*a* coming from a gas supply tube 106. The mixture containing nebulized particles 112 and breathing gas 114*b* is delivered to the patient via prongs 110 of cannula 102. In conventional prior art systems like this one, the particles are subject to turbulence within the device and have a long residence time in the large holding volume of the device. Rainout may occur in that arrangement.

SUMMARY

Devices and methods are provided herein for delivery of nebulized drug therapy to a patient via an integrated cannula and nebulizer. These devices and methods are particularly helpful for delivery of nebulized drugs, particularly sticky drugs delivered by surfactant, concurrently with high flow gas therapy (high volumetric flow, high velocity, or both) in a manner with reduced or no rain-out, without orientation effects, and with higher efficiency and entrainment than conventional systems. For example, the configurations described herein enable 50% or more entrainment of nebulized particles in breathing gas, where 50% or more of emitted nebulized particles are entrained in the gas and are therefore available to be delivered to the patient. This can be beneficial for high velocity systems (or high flow generally) that deliver breathing gas through small bore nasal cannulas and rely on high velocity or high flow administration of breathing gas for efficient oxygen delivery and/or carbon dioxide flushing, because it can deliver drugs efficiently and simultaneously with the breathing gas despite higher likelihood of turbulence by optimizing the fluid dynamics at the site of nebulized drug introduction and along the drug/gas delivery flow path.

The improved drug entrainment effect can be facilitated by an integrated cannula and nebulizer. In this integrated device, the nebulizer is positioned to emit nebulized particles directly into the cannula such that breathing gas and nebulized medicament mix within the cannula body, rather than upstream of the cannula, obviating the need to flow the gas and medicament mixture within a delivery tube or external mixing chamber. The nebulizer may be integrated into the cannula, for example, by aligning the emission direction of the nebulizer with a parallel, axisymmetric flow of breathing gas and with the outlet of the cannula. By the flow being axisymmetric, streamlines of the flow are symmetrically located about the longitudinal axis of the nasal prong (in some instances, all streamlines are symmetrically located about the longitudinal axis). In one advantage, the nebulized particles can be emitted directly into the primary flow path of breathing gas which contains minimal or even no changes in direction once the nebulized particles are entrained, minimizing rain-out by obviating the need for a mixing chamber and adaptor and reducing the likelihood of particles contacting a surface. This configuration, emitting particles from the nebulizer directly into the primary gas flow path, contrasts with the conventional system which diverts breathing gas into a mixing chamber away from the primary flow path from delivery tube to cannula, and requires particles to travel a longer and more convoluted path between mixing and delivery to the patient. In comparison, directly emitting the particles into the primary gas flow path efficiently entrains the particles in the flow without diversion to a mixing chamber and minimizes the surfaces the particles may hit to prevent rain-out. Rain-out may be reduced by introducing the nebulized particles to the gas flow just before the gas exits the cannula, minimizing changes in direction and the distance the drug must travel inside a conduit where it could impinge on surfaces. Furthermore, using a remote drug reservoir can reduce or eliminate the need for a large reservoir on the cannula, and the incorporation of the nebulizer with the cannula can reduce or eliminate the need for adapter features, thus reducing size and contributing to an overall configuration, when combined with the absence of a diversionary mixing chamber, that is lighter, less bulky, and more comfortable for the patient. Thus, the cannula-integrated nebulizer described herein improves efficiency of drug delivery by reducing rain-out and improving entrainment of particles into the gas flow, while also increasing patient comfort with reduced size relative to conventional cannula and nebulizer systems.

In one aspect, provided herein is a system for providing respiratory therapy to a patient comprising a nasal cannula having a cannula body, an inlet tube (e.g., first and second inlet tubes), and a nasal prong for the delivery of a flow of breathing gas to the patient, the flow of breathing gas supplied to the cannula body via the inlet tube, the nasal prong having a longitudinal axis, an inlet in fluid communication with the cannula body, and an outlet for insertion into the nare of the patient. The system further includes a nebulizer adapted to receive a liquid medicament and having an aerosol generator operable to generate a flow of aerosolized medicament from the liquid medicament for delivery to the breathing gas so as to achieve improved entrainment. In some adaptations, the aerosol generator is positioned along and centered on the longitudinal axis of the nasal prong and can generate the medicament flow along that longitudinal axis. The medicament mixes with the flow of breathing gas by aligning the emission direction of the nebulizer with a parallel, axisymmetric flow of breathing gas and with the outlet of the cannula, and by directing the breathing gas symmetrically into the nasal prong with a curved flow path configured to entrain the medicament with a slipstream effect. The system may include a flow director adapted to receive the flow of breathing gas and direct it into the nasal prong.

In some implementations, the flow director has multiple portions to help facilitate the mixing with the nebulized medicament. For example, the flow director may have a first portion coupled to the cannula body and a second portion coupled to the nebulizer so that breathing gas can flow into the nasal prong along a desired path so as to be positioned to efficiently receive the aerosolized medicament. In application, such an arrangement may be configured so that the first portion is positioned to receive the flow of breathing gas from the inlet tube and direct the flow of breathing gas into the nasal prong such that the breathing gas flows along the longitudinal axis, and the second portion secured to the nebulizer and configured such that the flow of aerosolized medicament is contained within the flow of breathing gas as it moves along the longitudinal axis of the nasal prong for delivery to the patient. The second portion can be positioned at the entry point in the nasal prong where the breathing gas enters, or slightly proximal from that point, or be integrally formed with that point, the point chosen so as to effect the entrainment of medicament via a slipstream effect enabled by directing the breathing gas in an axisymmetric manner with controlled velocity and direction parallel with the nasal prong and thereby form the combined flow so that entrainment is as efficient as possible. This system for delivery of aerosolized medicament with a respiratory therapy is advantageous over conventional systems because it can generate a generally parallel and concentrated flow of aerosol entrained in breathing gas with minimal to no rain-out or orientation effects, and with higher efficiency and entrainment. The system has improved patient comfort relative to conventional designs by reducing bulk on the cannula itself through the use of a remote drug reservoir.

In some implementations, the breathing gas flows into the nasal prong along a path having a breathing gas axis that is symmetric along the longitudinal axis of the nasal prong. The flow director may form an annular gap between the inlet of the nasal prong and the nebulizer. The flow director may be configured such that the flow of breathing gas has its largest pressure drop in the nasal cannula across the annular gap relative to the other parts of the flow path in the nasal cannula. For example, the pressure drop in the flow of breathing gas across the annular gap is at least 30%. The flow of breathing gas may be delivered through the annular gap with a constant flow velocity along the annular gap. In some implementations, the aerosol generator is positioned along the longitudinal axis of the nasal prong at a point at which the flow of breathing gas has a theoretical zero flow rate. The point of theoretical zero flow rate is an advantageous position to introduce the flow of aerosolized medicament into the breathing gas, because the low, if not zero, flow rate and low likelihood of turbulence at that point allows for efficient entrainment of the aerosolized medicament into the breathing gas with approximately no radial directional bias. The space at or around the point of zero theoretical flow rate can be considered a mixing zone for the aerosol and breathing gas. The flow of breathing gas is axisymmetric about the longitudinal axis of the nasal prong up to the point of theoretical zero flow rate, after which the flow is axially oriented with respect to the longitudinal axis of the nasal prong due to the shape of the flow director symmetrically guiding the axisymmetric flow towards the nasal prong outlet. The flow of breathing gas about the longitudinal axis of the nasal prong up to the point of theoretical zero flow rate may be radial, substantially radial or directed towards the longitudinal axis. The flow of breathing gas about the longitudinal axis of the nasal prong up to the point of theoretical zero flow rate may form a shape that is any one of conical, hyperbolic, parabolic and circular.

In some implementations, the flow director includes an anti-rotation element which prevents rotation of the flow of breathing gas within the cannula body as it is supplied to the cannula body via the first and second inlet tubes. The anti-rotation element may comprise a plurality of baffles symmetrically arranged about the flow director, for example positioned around an outer wall of the flow director, near the junctions between the cannula and the first and second inlet tubes, or around an inner wall of the cannula body. In some implementations, the first and second inlet tubes are symmetrically arranged about the cannula body and directed towards the longitudinal axis of the nasal prong. In some implementations, the nasal prong has a hyperbolic or parabolic cross section. In some implementations, the nebulizer is removably attached to the flow director. The flow director may be coupled to the cannula body via an interference fit. The flow director may be coupled to the inlet of the nasal prong. In some implementations, the flow director is integrally formed in the cannula and/or the nasal prong.

In some implementations, the aerosol generator uses a vibrating mesh. The vibrating mesh is the part of the aerosol generator where aerosolized particles are emitted. The particles are emitted from the vibrating mesh in a certain direction with a mean particle velocity, so it may be advantageous to align the direction and mean particle velocity with the longitudinal axis of the nasal prong, along which the breathing gas is also directed by the flow director, so that the particles and breathing gas flow in the substantially same direction to produce a parallel and concentrated flow of breathing gas containing entrained aerosolized medicament. In some implementations, the flow of aerosolized medicament is emitted from an outer surface of the aerosol generator, where the outer surface is centered along the longitudinal axis of the nasal prong. For example, the vibrating mesh is aligned with the outlet of the nasal prong. The flow of aerosolized medicament may be emitted from the vibrating mesh at the point of theoretical zero flow rate of breathing gas. The vibrating mesh is attached to a piezoelectric element that may be in electrical contact with a controller on a printer circuit board, for example, via spring contact pins. The system may be powered and/or controlled via wires that are in electrical contact with the printed circuit board for the provision of electrical signals from a signal generator to the vibrating mesh. The wires may be threaded through the first and/or second inlet tubes of the nasal cannula. In some implementations, a housing is attached to the cannula body. The housing may comprise injection molded plastic and may be attached to the cannula body using a snap-fit connection. In some implementations, the housing contains O-rings to achieve a liquid tight seal between the vibrating mesh and the housing. In some implementations, the housing contains a reservoir filled with liquid medicament, the reservoir arranged such that the liquid medicament is in contact with an inner surface of the vibrating mesh. The reservoir is in fluid communication with a liquid feed line which may be threaded through the first and/or second inlet tubes of the nasal cannula. The liquid feed line may comprise micro-bore tubing.

In some implementations, the first and second inlet tubes are each coupled to a supply tube for fluidic communication with a source of breathing gas. In some implementations, the cannula comprises a soft rubber, a rubber-like material, molded silicone, a thermoplastic elastomer (TPE), or dip molded polyvinyl chloride (PVC). In some implementations, the flow director comprises an injection molded plastic. In some implementations, the medicament comprises at least one of: bronchodilators, surfactants and antibiotics. For example, the liquid medicament comprises at least one of: Albuterol (Ventolin), Salbutamol (Proventil), Levosalbutamol/Levalbuterol (Xopenex), Curosurf (Chiesi Pharmaceuticals), Alveofact (Boehringer Ingelheim), Survanta (Abbott Laboratories), Exosurf (Glaxo Wellcome), Surfaxin (Discovery Laboratories), macrolides, erythromycin, clarithromycin, azithromycin, glycopeptides, vancomycin, teicoplanin, oxazolidinone, quinupristin/dalfopristin, aminoglycosides, gentamicin, tobramycin, amikacin, streptomycin, netilmicin, quinolones, ciprofloxacin, ofloxacin, levofloxacin, tetracyclines, oxytetracycline, doxycycline, minocycline, cotrimoxazole, colistin, imipenem, meripenim, pumactant, lucinactant, poractant alfa, beractant, calfactant, Beraksurf, Venticute, and colfosceril palmitate.

In another aspect, provided herein is a method of providing respiratory therapy to a patient. The method comprises a first step of providing a flow of breathing gas to a cannula having a cannula body, first and second inlet tubes, and a nasal prong, the flow of breathing gas supplied to the cannula body via the first and second inlet tubes, the nasal prong having a longitudinal axis, an inlet in fluid communication with cannula body, and an outlet for insertion into the nare of the patient. The method further comprises the step of directing the flow of the breathing gas using a flow director contained within the cannula body such that the breathing gas flows along the longitudinal axis of the nasal prong. The method further comprises the step of providing a flow of aerosolized medicament to the cannula from a nebulizer having a aerosol generator positioned along and centered on the longitudinal axis, the aerosol generator configured to generate the flow of aerosolized medicament from a liquid medicament. The method further comprises the step of delivering the flow of breathing gas and the flow of aerosolized medicament to the nare of the patient via the nasal prong, the flow of aerosolized medicament contained within the flow of breathing gas as it moves along the longitudinal axis of the nasal prong towards the nare of the patient. This method for delivery of aerosolized medicament with a respiratory therapy is advantageous over conventional systems by generating a generally parallel and concentrated flow of aerosol entrained in breathing gas without rain-out, without orientation effects, and with higher efficiency and entrainment. The method is also better for patient comfort by reducing bulk on the cannula itself with adaptability with a remote drug reservoir. The method may employ the system of the first aspect, including any of its specific implementations or examples.

In some implementations, the method further comprises directing the flow of breathing gas into the nasal prong along a path having a breathing gas axis that is symmetric along the longitudinal axis of the nasal prong. In some implementations, the method further comprises forming an annular gap between an inlet of the nasal prong and the nebulizer. The flow director may be configured such the flow of breathing gas has a largest pressure drop in the nasal cannula across the annular gap. For example, the pressure drop in the flow of breathing gas across the annular gap is at least 30%. The flow of breathing gas may pass through the annular gap with the same flow velocity at any point along the annular gap.

In some implementations, the method further comprises positioning the aerosol generator along the longitudinal axis at a point at which the flow of breathing gas has a theoretical zero flow rate. The flow of breathing gas is axisymmetric about the longitudinal axis of the nasal prong up to the point of theoretical zero flow rate, after which the flow is axially orientated with respect to the longitudinal axis of the nasal prong. The flow of breathing gas along the longitudinal axis of the nasal prong up to the point of theoretical zero flow rate may be radial, substantially radial or directed towards the longitudinal axis. The flow of breathing gas along the longitudinal axis of the nasal prong up to the point of theoretical zero flow rate may form a shape that is any one of conical, hyperbolic, parabolic and circular.

In some implementations, the method further comprises preventing rotation of the flow of breathing gas from the first and second inlet tubes via an anti-rotation element. The anti-rotation element may comprise a plurality of baffles symmetrically arranged about the flow director, for example, positioned around an outer wall of the flow director, near the junctions between the cannula and the first and second inlet tubes, or around an inner wall of the cannula body. In some implementations, the method further comprises arranging the first and second inlet tubes symmetrically about the cannula body, and directing the first and second inlet tubes towards the longitudinal axis of the nasal prong.

In some implementations, the method further comprises providing an electric signal to the aerosol generator of the nebulizer via a wire to enable aerosolization of the liquid medicament. The aerosol generator comprises a vibrating mesh. In some implementations, the method further comprises connecting the source of breathing gas to the first and second inlet tubes of the nasal cannula via a delivery tube. In some implementations, the method further comprises supplying the liquid medicament to the nebulizer from a supply bag via a feed line comprising micro-bore tubing. The medicament may comprise at least one of: bronchodilators, surfactants and antibiotics. For example, the medicament comprises at least one of: Albuterol (Ventolin), Salbutamol (Proventil), Levosalbutamol/Levalbuterol (Xopenex), Curosurf (Chiesi Pharmaceuticals), Alveofact (Boehringer Ingelheim), Survanta (Abbott Laboratories), Exosurf (Glaxo Wellcome), Surfaxin (Discovery Laboratories), macrolides, erythromycin, clarithromycin, azithromycin, glycopeptides, vancomycin, teicoplanin, oxazolidinone, quinupristin/dalfopristin, aminoglycosides, gentamicin, tobramycin, amikacin, streptomycin, netilmicin, quinolones, ciprofloxacin, ofloxacin, levofloxacin, tetracyclines, oxytetracycline, doxycycline, minocycline, cotrimoxazole, colistin, imipenem, meripenim, pumactant, lucinactant, poractant alfa, beractant, calfactant, Beraksurf, Venticute, and colfosceril palmitate.

In another aspect, provided herein is a system for delivery of breathing gas and aerosolized medicament to a patient. The system comprises a delivery tube configured to supply a flow of breathing gas; a nebulizer configured to supply a flow of nebulized medicament; and a nasal interface having a first inlet, a second inlet, a mixing chamber in fluid communication with the first inlet and the second inlet, and an outlet in fluid communication with the mixing chamber to deliver a mixed flow of breathing gas and nebulized medicament. The first inlet is coupled to a distal end of the delivery tube to receive the flow of breathing gas into the mixing chamber, and the second inlet is coupled to an emitter of the nebulizer to receive the flow of nebulized medicament directly into the mixing chamber. The mixing chamber and the second inlet are aligned with a longitudinal axis of the outlet, such that mixing of the flow of breathing gas and the flow of nebulized medicament occurs directly behind the outlet and along a direction coaxial with the longitudinal axis. For example, the breathing gas flows into the outlet along a path having a breathing gas axis that is symmetric along the longitudinal axis. The medicament mixes with the flow of breathing gas by aligning the emission direction of the nebulizer with a parallel, axisymmetric flow of breathing gas and with the outlet of the cannula, and by directing the breathing gas symmetrically into the nasal prong with a curved flow path configured to entrain the medicament with a slipstream effect. This system for delivery of aerosolized medicament with a respiratory therapy is advantageous over conventional systems because it can generates a generally parallel and concentrated flow of aerosol entrained in breathing gas with minimal to no out rain-out, without or orientation effects, and with higher efficiency and entrainment. The system has improved patient comfort relative to conventional designs by reducing bulk on the cannula itself through the use of a remote drug reservoir.

In some implementations, the outlet is a nasal prong. The nasal prong may have a hyperbolic or parabolic cross section. In some implementations, the breathing gas flows into the outlet along a path having a breathing gas axis that is symmetric along the longitudinal axis.

In some implementations, the nasal interface further comprises a flow director having a first portion and a second portion, the first portion coupled to the cannula body and adapted to receive the flow of breathing gas from the first inlet and direct the flow of breathing gas into the mixing chamber such that the breathing gas flows along the longitudinal axis, and the second portion secured to the nebulizer and configured such that the flow of nebulized medicament is contained within the flow of breathing gas as it moves along the longitudinal axis of the outlet for delivery to the patient. The flow director may form an annular gap along a breathing gas flow path between the first inlet and the mixing chamber. The flow of breathing gas may have a pressure drop in the nasal interface that is largest across the annular gap. For example, the pressure drop in the flow of breathing gas across the annular gap is at least 30%. The flow of breathing gas may pass through the annular gap with a flow velocity that is constant at any point along the annular gap. In some implementations, the flow director further comprises an anti-rotation element which prevents rotation of the flow of breathing gas within the nasal interface as it is supplied via the first inlet. For example, the anti-rotation element comprises a plurality of baffles symmetrically arranged about the flow director.

In some implementations, the second inlet is positioned along the longitudinal axis at a point at which the flow of breathing gas has a theoretical zero flow rate. The flow of breathing gas may be axisymmetric about the longitudinal axis of the nasal prong up to the point of theoretical zero flow rate, after which the flow is axially orientated with respect to the longitudinal axis. For example, the flow of breathing gas about the longitudinal axis up to the point of theoretical zero flow rate is radial, substantially radial or directed towards the longitudinal axis. For example, flow of breathing gas about the longitudinal axis of the nasal prong up to the point of theoretical zero flow rate forms a shape that is any one of conical, hyperbolic, parabolic and circular.

In some implementations, the emitter uses a vibrating mesh. The vibrating mesh is the part of the emitter where nebulized particles are emitted. The particles are emitted from the vibrating mesh in a certain direction with a mean particle velocity, so it may be advantageous to align the direction and mean particle velocity with the longitudinal axis of the outlet, along which the breathing gas is also directed, so that the particles and breathing gas flow in the substantially same direction to produce a parallel and concentrated flow of breathing gas containing entrained nebulized medicament. In some implementations, the flow of aerosolized medicament is emitted from an outer surface of the aerosol generator, where the outer surface is centered along the longitudinal axis of the nasal prong. The vibrating mesh is attached to a piezoelectric element that may be in electrical contact with a controller on a printer circuit board, for example, via spring contact pins. The system may be powered and/or controlled via wires that are in electrical contact with the printed circuit board for the provision of electrical signals from a signal generator to the vibrating mesh. The wires may be threaded through the first and/or second inlet tubes of the nasal cannula. In some implementations, a housing is attached to the nasal interface. The housing may comprise injection molded plastic and may be attached to the nasal interface using a snap-fit connection. In some implementations, the housing contains O-rings to achieve a liquid tight seal between the vibrating mesh and the housing. In some implementations, the housing contains a reservoir filled with liquid medicament, the reservoir arranged such that the liquid medicament is in contact with an inner surface of the vibrating mesh. The reservoir is in fluid communication with a liquid feed line which may be threaded through the delivery tube. The liquid feed line may comprise micro-bore tubing.

In some implementations, the delivery tube is in fluidic communication with a source of breathing gas. In some implementations, the nasal interface comprises a soft rubber, a rubber-like material, molded silicone, a thermoplastic elastomer (TPE), or dip molded polyvinyl chloride (PVC). In some implementations, the medicament comprises at least one of: bronchodilators, surfactants and antibiotics. For example, the liquid medicament comprises at least one of: Albuterol (Ventolin), Salbutamol (Proventil), Levosalbutamol/Levalbuterol (Xopenex), Curosurf (Chiesi Pharmaceuticals), Alveofact (Boehringer Ingelheim), Survanta (Abbott Laboratories), Exosurf (Glaxo Wellcome), Surfaxin (Discovery Laboratories), macrolides, erythromycin, clarithromycin, azithromycin, glycopeptides, vancomycin, teicoplanin, oxazolidinone, quinupristin/dalfopristin, aminoglycosides, gentamicin, tobramycin, amikacin, streptomycin, netilmicin, quinolones, ciprofloxacin, ofloxacin, levofloxacin, tetracyclines, oxytetracycline, doxycycline, minocycline, cotrimoxazole, colistin, imipenem, meripenim, pumactant, lucinactant, poractant alfa, beractant, calfactant, Beraksurf, Venticute, and colfosceril palmitate.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which:

FIGS. 3A and 3B show a nasal cannula having an internally mounted nebulizer and flow director, according to an illustrative implementation;

DETAILED DESCRIPTION

To provide an overall understanding of the assemblies and methods described herein, certain illustrative implementations will be described. Although the implementations and features described herein are specifically described for high velocity respiratory therapy, it will be understood that all the components and other features outlined below may be combined with one another in any suitable manner and may be adapted and applied to other respiratory therapy systems and devices, including low flow oxygen therapy, continuous positive airway pressure therapy (CPAP), mechanical ventilation, oxygen masks, Venturi masks, and Tracheostomy masks.

The term "about," as used herein, should be understood to mean plus or minus 20%. For example, "about 20 mm" should be understood to mean 20 mm±4 mm. The term "emitter" as used herein should be understood to be any device or feature capable of outputting aerosolized or nebulized particles, for example, drug particles, and may be used interchangeably with "aerosol generator". An "emitter" may be used to specifically refer to a part of a nebulizer where nebulized particles are ejected. The terms "aerosolized" and "nebulized", "nebulization" and "aerosolization", or "aerosolize" and "nebulize" may be used interchangeably to refer to products or processes involving a liquid or solid composed of finely divided particles suspended in a gaseous medium. Nebulizers described herein may use a vibrating mesh attached to a piezoelectric element to generate fine particles; however, other suitable types of nebulizers may be employed.

Exemplary drugs/medicaments for nebulization include bronchodilators, surfactants (for example surfactants carrying drugs such as those listed below), and antibiotics. For example, the drug/medicament used herein may be any one of Albuterol (Ventolin), Salbutamol (Proventil), Levosalbutamol/Levalbuterol (Xopenex), Curosurf (Chiesi Pharmaceuticals), Alveofact (Boehringer Ingelheim), Survanta (Abbott Laboratories), Exosurf (Glaxo Wellcome), Surfaxin (Discovery Laboratories), macrolides, erythromycin, clarithromycin, azithromycin, glycopeptides, vancomycin, teicoplanin, oxazolidinone, quinupristin/dalfopristin, aminoglycosides, gentamicin, tobramycin, amikacin, streptomycin, netilmicin, quinolones, ciprofloxacin, ofloxacin, levofloxacin, tetracyclines, oxytetracycline, doxycycline, minocycline, cotrimoxazole, colistin, imipenem, meripenim, pumactant, lucinactant, poractant alfa, beractant, calfactant, Beraksurf, Venticute, colfosceril palmitate, and any other drug physically capable of being nebulized.

Figure 1:
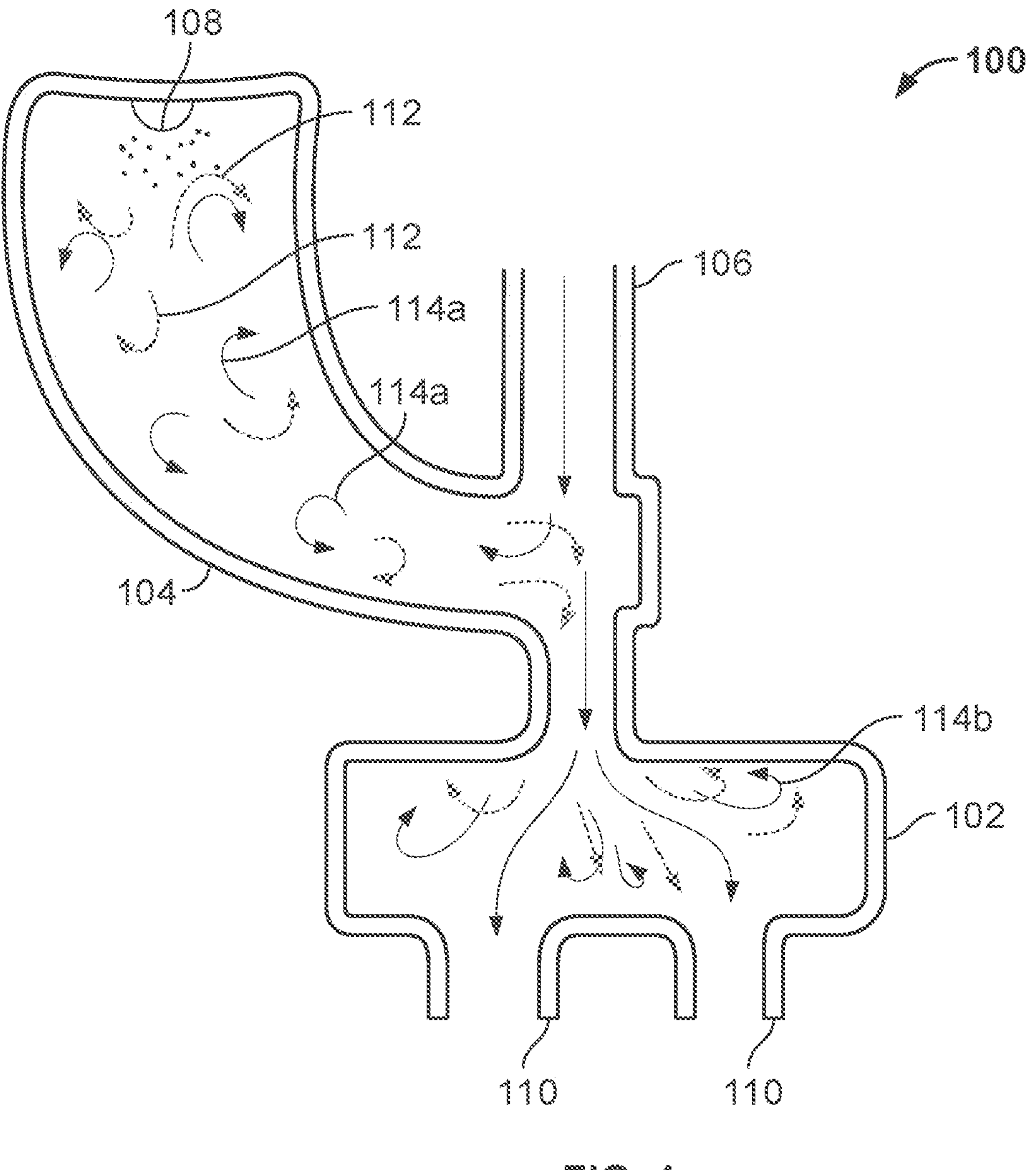
FIG. 1 shows a prior art nasal cannula with a nebulizer mixing chamber, according to an illustrative implementation.

The systems and methods provide the technical advance of being able to introduce nebulized particles (particularly sticky drugs that are carried by surfactants) into a high velocity flow of breathing gas, with minimal to no rainout. To reduce rain-out, the collection of particles on internal walls of the device used to deliver the breathing gas and nebulized particles, the introduction is made as close as possible to the exit point of the delivery device where the breathing gas is transferred to a patient. For nasal administration, this exit point is typically one or more prongs of a nasal cannula. FIG. 1 shows a conventional system 100 of the prior art where a mixing chamber 104 is positioned behind a cannula 102 for entrainment of nebulized particles 112 (shown as dots and checkered arrows) into breathing gas 114*a*. An emitter or nebulizer 108 is positioned to emit the nebulized particles 112 into mixing chamber 104 where the nebulized particles 112 mixing with breathing gas 114*a* delivered into mixing chamber 104 by gas supply tube 106. After mixing for some period of time, breathing gas 114*b* with entrained nebulized particles flows into cannula 102 and is delivered into the nares of a patient via prongs 110.

The velocity of gas 114*a* slows within the mixing chamber 104 due to the larger diameter of the mixing chamber 104; however, the particle flows 112 are still subject to turbulence, a long residence time, and a large holding volume that are likely to induce rain-out. This rain-out must be collected or it will be delivered to the patient. Any rain-out that is collected or otherwise not delivered to the patient reduces the amount of drug that is delivered to the patient. Furthermore, the mixing chamber 104 adds unwanted bulk to the cannula when positioned so close. These drawbacks stem from the requirement of the aerosol generator 108 and cannula 102 being separate devices connected via an adaptor. A generic aerosol generator is typically large enough to include a feature that will connect to standard fittings, an electrical connector, a drug reservoir, and the aerosol generating element. The result is a device that is inherently too large to attach directly to a cannula and which must be configured so that the generated aerosol is introduced into a location along the breathing gas flow path that is characterized by a high velocity relative to the low velocity within the mixing chamber. To do this, some sort of positioning system must be used to support the device and all of the rain out must be sent into the patient.

Figure 2A:
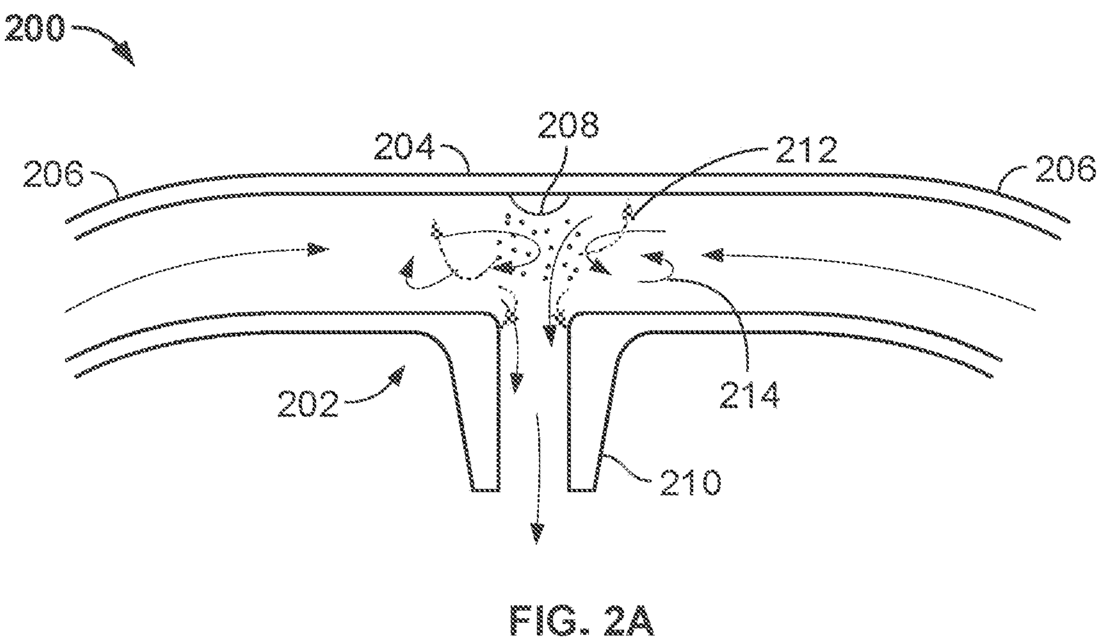
FIGS. 2A-2D show various nasal cannulas having an integrated nebulizer, according to illustrative implementations.
Figure 2B:
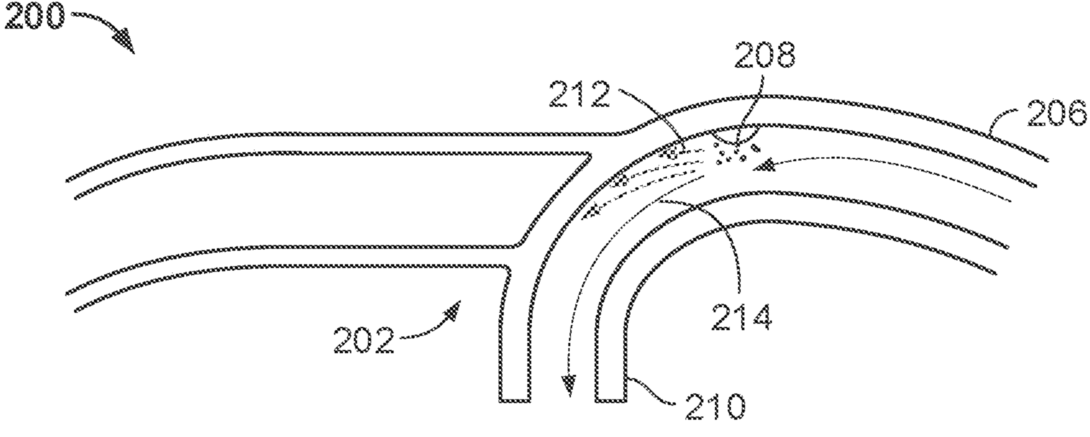
Figure 2C:
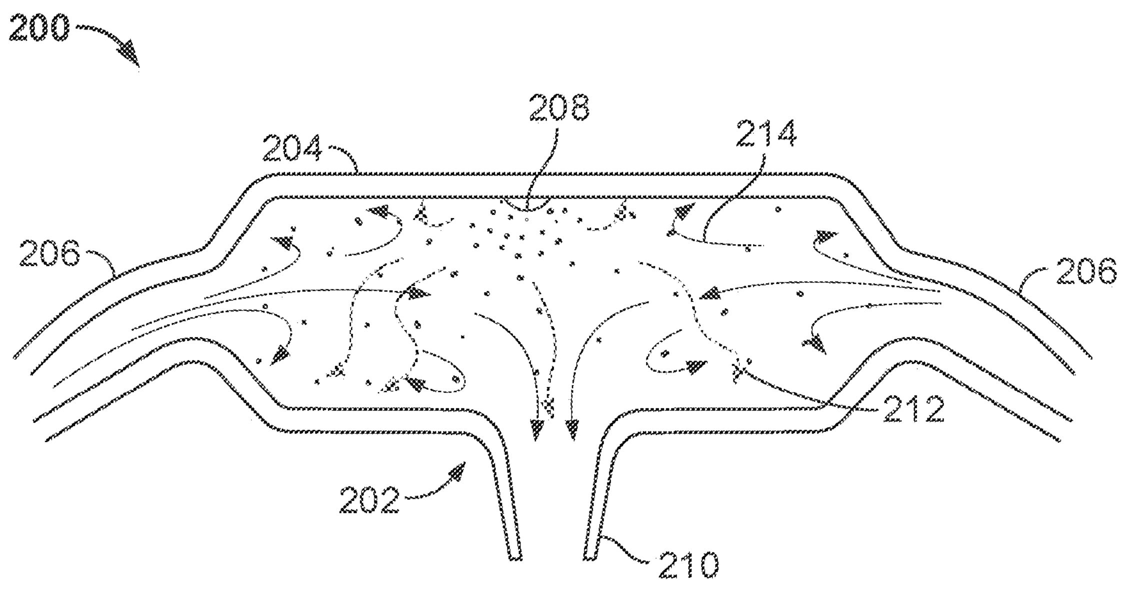
Figure 2D:
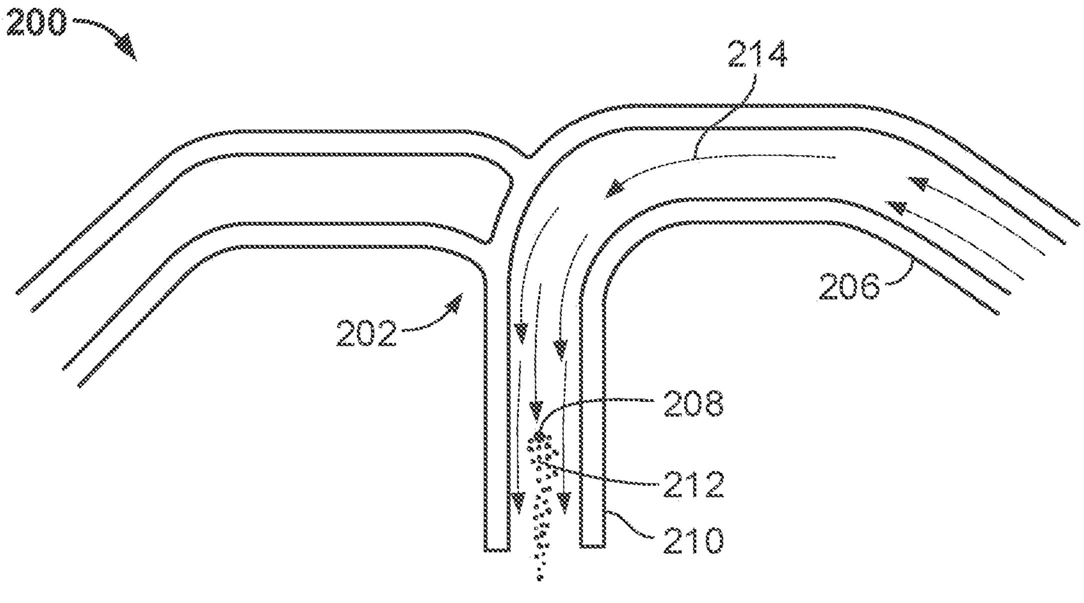

The systems and methods disclosed herein include an integrated cannula and nebulizer to address these and other shortcomings of conventional designs. For example, nebulized particles are generated directly into the primary flow path. The particles are emitted in a certain direction with a mean particle velocity, so it may be advantageous to align the direction and mean particle velocity with the longitudinal axis of the nasal prong, along which the breathing gas is also directed by the flow director, so that the particles and breathing gas flow in the substantially same direction to produce a parallel and concentrated flow of breathing gas containing entrained aerosolized medicament. Further, a remote drug reservoir may be used and thereby eliminate the need for a large or bulky reservoir attached to the cannula, and thereby obviate the need for adapter features, thus reducing size and reducing the overall fluid contacting interface that can otherwise lead to rainout. FIGS. 2A-2D depict several cannula geometries that allow mixing of the aerosolized particles directly into the gas flow path within the cannula. The first device 200 shown in FIG. 2A includes a cannula 202 having a vestibule 204 and one prong 210 (2 prongs is also possible). Breathing gas 214 enters vestibule 204 from gas supply tubes 206 and mixes with nebulized particles 212 (shown as dots and checkered arrows) from emitter 208 positioned at the vestibule 204. In this configuration, turbulence in the vestibule 204 and entrance to the prong 219 is likely to cause particles 212 to collide with the wall of the cannula 202 leading to rain out. The second device 200 shown in FIG. 2B includes an emitter 208 located along the wall of the cannula 202 to entrain the nebulized particles 212 in the breathing gas 214 as the gas 214 changes direction from gas supply tube 206 to prong 210. In this case, the particles 212 are ejected near the wall, and the change in flow direction is likely to drive the particles 212 into the wall. The third device 200 shown in FIG. 2C shows a cannula 202 with a larger vestibule 204 to allow the flow of gas 214 from gas supply tubes 206 to decelerate in the vestibule 204 before mixing with nebulized particles 212 from emitter 208 positioned within the vestibule 204. In this case, the longer residence time, turbulence, and the entrance effects of the prong 210 are likely to cause rain-out, and the larger size of cannula 202 would be uncomfortable to the patient.

To avoid the above mentioned issues of cannula bulk and drug rain-out, particles can be emitted from a point directly along the centerline of a straight prong in which breathing gas 214 follows a laminar flow. This is demonstrated in FIG. 2D which shows a device 200 of a cannula 202 where an emitter 208 is positioned along the centerline of prong 210. Breathing gas 214 enters cannula 202 from gas supply tube 206 and follows a laminar flow path after turning into prong 210. Nebulized particles 212 are entrained within the breathing gas 214 as it follows a substantially straight flow path along the length of prong 210, minimizing the changes in flow direction of nebulized particles 212 and thus reducing the likelihood of rain-out. This configuration requires a very small emitter that is capable of fitting within a prong 210 which is small in internal diameter. Furthermore, the drug to be nebulized must be supplied to the emitter 208 from a drug reservoir, so a fluid connection (not shown) must be established and may interfere with the laminar nature of the breathing gas flow 214 in prong 210.

The present disclosure addresses the problems discussed above by accomplishing the following objectives: eliminating the need for a reservoir on the nebulizer; minimizing the size and weight of the nebulizer; minimizing the distance that a nebulized drug particle must travel inside a conduit; minimizing changes in direction the nebulized drug particles must undergo while in a conduit; eliminating large holding volumes; minimizing turbulence where the nebulized drug particles are introduced and after the nebulized drug particles are entrained in the breathing gas flow; and approximating a condition where the emitter is on the centerline of a laminar flow with no direction changes.

While each of the devices of FIGS. 2A-2D accomplishes one or more of these objectives, FIG. 3A shows an optimized flow path device 300 addressing all of the above objectives. A cannula 302 includes an emitter 308, a prong 310 for insertion into a nare of a patient, a flow director 318, and a casing 304. Prong 310 includes a longitudinal axis 316, and emitter 308 is positioned at the point where longitudinal axis 316 intersects casing 304. Cannula 302 receives breathing gas 314 from gas supply tubes 306, and the breathing gas 314 is directed into an annular gap 319 defined by the space between casing 304 and a lip of flow director 318. By constraining the flow of gas through annular gap 319, flow director 318 directs the flow in a radial direction towards longitudinal axis 316, wherein emitter 318 is positioned. The flow entering prong 310 is substantially axisymmetric, that is all streamlines of the flow are symmetrically located about the longitudinal axis of the nasal prong, such that the flow is not biased toward any one side of prong 310. Using liquid medicament, emitter 308 generates a flow of aerosolized medicament with velocity in the desired direction of the breathing gas flow along longitudinal axis 316. The particles 312 are never directed toward the walls of cannula 302; rather, the particles 312 are ushered into the center of cannula 302 along longitudinal axis 316, along which the particles 312 flow until exiting prong 310.

Device 300 includes certain features that allow axisymmetric flow to occur, particularly such that the breathing gas 314 flows into nasal prong 310 along a path having a breathing gas axis that is symmetric along longitudinal axis 316. The flow into the cannula 302 is coming from two separate tubes 306, so there is a tendency for the radial flow to be biased so that more flow comes from the direction of the tube outlets; however, by creating a small annular gap 319 around the inlet to the prong 310, the flow can be balanced to have similar magnitude from all directions. For example, the flow of breathing gas 314 passes through annular gap 319 with the same flow velocity at any point along annular gap 319. The annular gap 319 must be small enough that more than about 30%, and preferably as much as possible, of the pressure drop of the cannula 302 occurs in the annular gap 319. For example, the pressure drop across annular gap 319 is the largest pressure drop in the cannula 302. This ensures that the flow will pass through all portions of the annular gap 319 evenly, as any area with a tendency to have a higher flow rate would also have a higher pressure drop. This is shown in FIG. 3B depicting a cross-sectional view of device 300 along line B of FIG. 3A. This cross-section shows that annular gap 319, formed by flow director 318 and casing 304, directs the flow of breathing gas 314 axisymmetrically inwards towards emitter 308 positioned along longitudinal axis 316.

All of the flow vectors originating from annular gap 319 are meeting at longitudinal axis 316 of prong 310, so there is a point with very low flow rate along or near longitudinal axis 316. Theoretically, this point may have zero flow. Emitter 308 is positioned near or at this point, and particles 312 are never directed towards the walls of the cannula, because the flow is minimized and uniformly directed toward longitudinal axis 316. In some implementations, the flow of breathing gas 314 is axisymmetric about the longitudinal axis of the nasal prong up to the point of theoretical zero flow rate, after which the flow is axially orientated with respect to the longitudinal axis of the nasal prong. For example, the flow of breathing gas 314 up to the point of theoretical zero flow rate is radial, substantially radial or directed towards the longitudinal axis, or forms a shape that is any one of conical, hyperbolic, parabolic, and circular. Nasal prong 310 may have a hyperbolic or parabolic cross-section to further encourage axisymmetric flow via gradual acceleration of the flow.

The gas supply tubes 306 are also prone to induce rotational flow in the cylindrical portion of the body of cannula 302. Rotational flow is to be avoided, as it causes particles 312 to be moved to the outside walls of the conduit by centrifugal force. To prevent this, anti-rotation features (not shown), such as baffles, that resist rotational flow but allow flow in the axial direction can be employed, for example, around flow director 318. In some implementations, a plurality of baffles is symmetrically arranged around flow director 318, for example, positioned around an outer wall of the flow director 318, near the junctions between the cannula 302 and the gas supply tubes 306, or around an inner wall of the casing 304. The orientation of the tubes 306 can also be arranged so that the inlets of cannula 302 point toward the central axis 316 instead of being offset from it. If two equal-flow inlets are used, they can be positioned symmetrically opposite another about longitudinal axis 316 to cancel these effects, thus preventing rotational flow.

In some implementations, a medicament reservoir is in fluid communication with emitter 308. The medicament reservoir (not shown) may be directly attached to cannula 302, as is discussed further in relation to FIGS. 4A, 4B, and 5 below. Alternatively, the medicament reservoir is positioned remotely and connected to emitter 308 via a conduit. This implementation reduces bulk on the cannula, maintaining patient comfort. The conduit may be a liquid feed supply line integrated into or on one or both of gas supply tubes 306. Electrical lines for controlling emitter 308 may be integrated into or on one or both of gas supply tubes 306. These electrical lines may be connected to a capital unit which supplies the breathing gas 314 to gas supply tubes 306 and/or contains a processor configured to control the function of emitter 308. This may be particularly useful in feedback control of nebulization when certain physiological parameters are monitored during the administration of respiratory therapy and nebulized medicament. Such physiological parameters may include breathing patterns, inspiratory/expiratory ratio, oxygen level (blood oxygen saturation (SpO2) or fraction of inspired oxygen (FiO2)), carbon dioxide level, disease status, and disease stage.

Suitable sources of pressurized breathing gas will be known to one of ordinary skill in the art. For example, the source may be the Vapotherm Flowrest System, Vapotherm Palladium System, Precision Flow unit, or the Vapotherm 2000i, all of which are provided by Vapotherm, Inc. of Exeter, New Hampshire, USA. For example, the source may be the respiratory therapy systems described in U.S. patent application Ser. No. 16/901,902 and U.S. patent application Ser. No. 15/783,566 (U.S. Publication No. 2018/0104436), each of which is incorporated herein by reference in its entirety. Other suitable sources of breathing gas will be known to one of ordinary skill in the art from the description herein.

The source of breathing gas may be fluidically connected to gas supply tubes 306 via a delivery tube (not shown) comprising an inlet configured to receive breathing gas 314 from the source and a split outlet configured to divide and transmit breathing gas 314 into the flows of breathing gas 314 to each of gas supply tubes 306, respectively. Device 300 may be integrated in a respiratory therapy system having a breathing gas source and, optionally, a humidifying device (e.g., a vapor transfer unit or hotpot humidifier). Alternatively, device 300 may be implemented as an add-on unit configured to couple to any compatible respiratory therapy system with a breathing gas source and, optionally, a humidifying device (e.g., a vapor transfer unit or hotpot humidifier). Device 300 may be used with a system that provides heated and humidified breathing gas 314.

Suitable flowrates of breathing gas 314 range from about 1 L/min to about 80 L/min. In some implementations, the breathing gas flowrate and nasal prong inner diameter are chosen such that the exit velocity of breathing gas 314 from nasal prong 310 is at least about 40 m/s. In some implementations, the exit velocity is between about 40 m/s and about 75 m/s for a balance effective flushing of $CO_2$ from the patient airway and patient comfort or noise reduction. For example, prong 310 has an internal diameter of about 1.0 mm to about 4.0 mm.

Figure 4A:
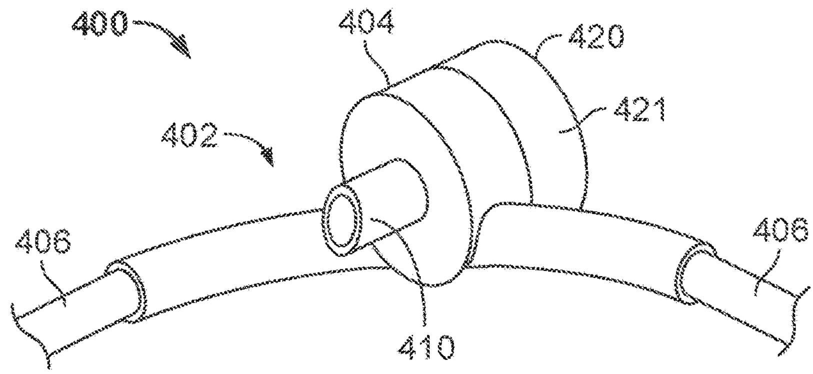
FIGS. 4A and 4B show assembled and exploded views of a nasal cannula having an internally mounted nebulizer and flow director, according to an illustrative implementation.
Figure 4B:
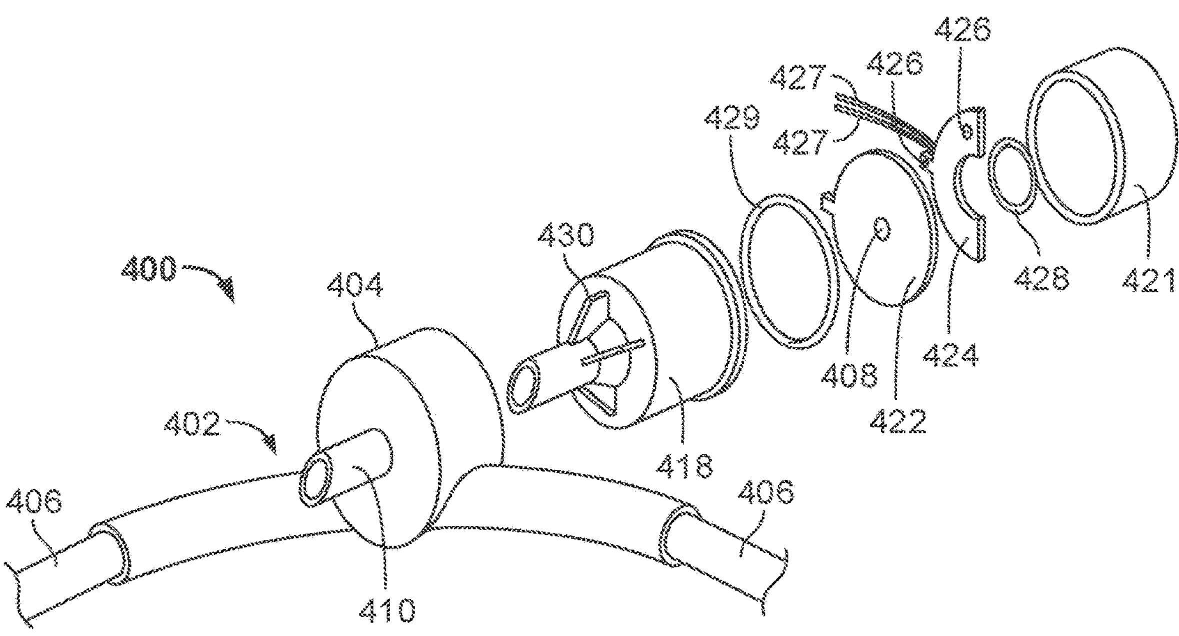

FIGS. 4A and 4B show another device 400 with cannula 402 configured to produce an axisymmetric radial flow for improved delivery of nebulized medicament. Cannula 402 has a cylindrical body 404 into which a nebulizer module 420 of similar diameter (e.g., between about 14 mm and 20 mm) connects such that nebulized medicament is ejected along the longitudinal axis defined by a prong 410 for insertion into a nare of a patient. As gas is delivered into cannula 402 by gas supply tubes 406, the gas is directed in an axisymmetric radial manner by a flow director 418 (not shown in FIG. 4A) positioned between prong 410 and nebulizer module 420. Nebulizer module 420 includes a housing 421 that couples the nebulizer module 420 to cylindrical body 404 of cannula 402.

FIG. 4B shows an exploded view of device 400 showing all the components contained within cannula 402 and nebulizer module 420. As mentioned above, flow director 418 is positioned within body 404 between prong 410 and nebulizer module 420. Flow director 418 includes anti-rotation baffles 430 that resist rotational flow but allow flow in the axial direction, for example, around flow director 418 before entering the annular gap formed between flow director 418 and nebulizer module 420. Baffles 430 are symmetrically arranged around flow director 418.

Nebulizer module 420 includes an emitter 408 embedded in a piezoelectric ring 422, a printed circuit board 424 having spring pin contacts 426, wire leads 427 connected to printed circuit board 424, a first O-ring 428, and a second O-ring 429. First O-ring 428 seals the piezoelectric ring 422 against housing 421, and second O-ring 429 seals piezoelectric ring 422 against flow director 418. Spring pin contacts 426 allow a signal that is sent through wire leads 427 to be conducted to piezoelectric ring 422 (e.g., from a signal generator). Alternatively, wire leads 427 could be soldered directly to printed circuit board 424, or spring pin contacts 426 could be attached directly to wire leads 427 and positioned to contact piezoelectric ring 422. Emitter 408 is a vibrating mesh that is configured to vibrate at a frequency when an electric signal is applied to piezoelectric ring 422, such that medicament is nebulized and emitted from emitter 408 when in contact with the vibrating mesh of emitter 408.

Nebulizer module 420 may be configured to be removably attached to flow director 418 or cylindrical body 404 of cannula 402. For example, housing 421 attaches to cannula 402 using a snap-fit connection, a magnetic connection, or a twist-lock connection. Flow director 418 may be shaped to have an interference fit with cylindrical body 404 inside prong 410 and around the inside of the cylindrical body 404. This configuration ensures a leak-free interface between the components when nebulizer module 420 is plugged into cannula 402. Flow director 418 may be configured to couple to the inlet of prong 410. O-rings 428 and 429 may be configured to enable liquid-tight seals, further ensuring a leak-free interface.

The gas supply tubes 406 are shown in FIGS. 4A and 4B to be unsymmetrical about the longitudinal axis of prong 410, so the tubes 406 are prone to induce rotational flow in the cylindrical body 404 of cannula 402. Rotational flow is to be avoided, as it causes particles to be moved to the outside walls of the conduit by centrifugal force. To prevent this, anti-rotation baffles 430 that resist rotational flow but allow flow in the axial direction are employed around flow director 418. In some implementations, at least 1, 2, 3, 4, 5, or 6 baffles are positioned around flow director 418. Although FIGS. 4A and 4B show supply tubes 406 being routed to either side of cannula 402 (e.g., as lariat tubes wrapped around a patients cars), it is to be understood that one or more gas supply tubes may alternatively be plugged into cannula 402 from behind or next to nebulizer 420 such that the flow within the tubes is parallel with prong 410.

In some implementations, a medicament reservoir is in fluid communication with emitter 408. The medicament reservoir (not shown) may be contained within housing 421 of nebulizer module 420, as is discussed further in relation to FIG. 5 below. Alternatively, the medicament reservoir is positioned remotely and connected to nebulizer module 420 via a fluid conduit (e.g., micro-bore tubing). This implementation reduces bulk on the cannula, maintaining patient comfort. For example, the medicament reservoir is contained within a capital unit having a fluid pump configured to pump the medicament to nebulizer module 420 via the fluid conduit. The fluid conduit may be a liquid feed supply line integrated into or on one or both of gas supply tubes 406. Wire leads 427 may be integrated into or on one or both of gas supply tubes 306. For example, wire leads 427 and/or a fluid supply line are routed inside one or both of gas supply tubes 406, are co-extruded with gas supply tubes 406 so as to be embedded inside the walls of the tubing (e.g., to form e-tubing), affixed externally to gas supply tubes 406 by spiraling around the tubing, adhesives, clips, or another attachment method, or are routed entirely separately from gas supply tubes 406. In some implementations, breathing gas 414 only enters cannula 420 from one of gas supply tubes 406 while the other contains only wire leads 427 and the medicament supply line. In some implementations, cannula 502 includes a 3-to-1 valve for inlets of breathing gas 414, medicament, and electrical connection.

Wire leads 427 may be connected to a capital unit which supplies the breathing gas 414 to gas supply tubes 406 and/or contains a processor configured to control the function of nebulizer module 420. This may be particularly useful in feedback control of nebulization when certain physiological parameters are monitored during the administration of respiratory therapy and nebulized medicament. Such physiological parameters may include breathing patterns, inspiratory/expiratory ratio, oxygen level (e.g., blood oxygen saturation (SpO2) or fraction of inspired oxygen (FiO2)), carbon dioxide level, disease status, and disease stage. For example, the capital unit, a controller, or a processor may send instructions to nebulizer module 420 via wire leads 427 to increase, decrease, turn on, or turn off nebulization based one or more physiological parameters. In some implementations, medicament is nebulized intermittently in synchronization with patient breathing detected via breath sensing, such that medicament is only delivered during patient inspiration.

Suitable sources of pressurized breathing gas will be known to one of ordinary skill in the art. For example, the source may be the Vapotherm Flowrest System, Vapotherm Palladium System, Precision Flow unit, or the Vapotherm 2000i, all of which are provided by Vapotherm, Inc. of Exeter, New Hampshire, USA. For example, the source may be the respiratory therapy systems described in U.S. patent application Ser. No. 16/901,902 and U.S. patent application Ser. No. 15/783,566 (U.S. Publication No. 2018/0104436), each of which is incorporated herein by reference in its entirety. Other suitable sources of breathing gas will be known to one of ordinary skill in the art from the description herein.

The source of breathing gas 414 may be fluidically connected to gas supply tubes 406 via a delivery tube (not shown) comprising an inlet configured to receive breathing gas 414 from the source and a split outlet configured to divide and transmit breathing gas 414 into the flows of breathing gas 414 to each of gas supply tubes 406, respectively. Device 400 may be integrated in a respiratory therapy system having a breathing gas source and, optionally, a humidifying device (e.g., a vapor transfer unit or hotpot humidifier). Alternatively, device 400 may be implemented as an add-on unit configured to couple to any compatible respiratory therapy system with a breathing gas source and, optionally, a humidifying device (e.g., a vapor transfer unit or hotpot humidifier). Device 400 may be used with a system that provides heated and humidified breathing gas 414.

Suitable flowrates of breathing gas 414 range from about 1 L/min to about 80 L/min. In some implementations, the breathing gas flowrate and nasal prong inner diameter are chosen such that the exit velocity of breathing gas 414 from nasal prong 410 is at least about 40 m/s. In some implementations, the exit velocity is between about 40 m/s and about 75 m/s for a balance effective flushing of $CO_2$ from the patient airway and patient comfort or noise reduction. For example, prong 410 has an internal diameter of about 1.0 mm to about 4.0 mm.

Any of flow director 418, housing 421, and cannula 402 may be manufactured by injection molding a material such as plastic. Alternatively, cannula 402 may be manufactured by coating or dip molding one or more mandrels with a material such as plastic. Suitable materials for cannula 402, flow director 418, and housing 421 include a soft rubber, a rubber-like material, molded silicone, a thermoplastic elastomer (TPE), or dip molded polyvinyl chloride (PVC).

Figure 5:
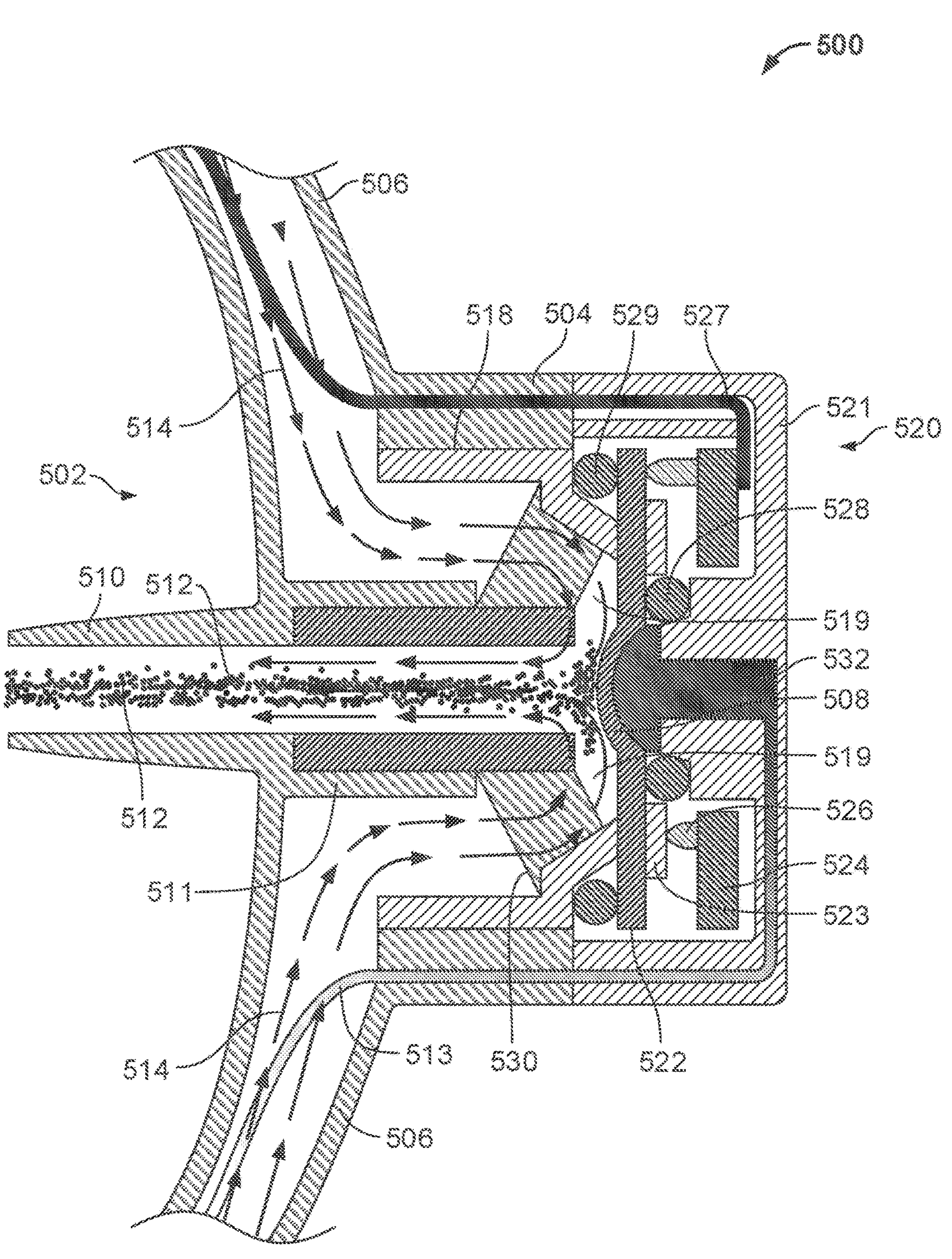
FIG. 5 shows a cross-section of a nasal cannula having an internally mounted nebulizer and flow director, according to an illustrative implementation.

FIG. 5 shows a cross-sectional view of a device 500 including a cannula 502 configured to produce an axisymmetric radial flow for improved delivery of nebulized medicament 512. Cannula 502 has a cylindrical body 504 into which a nebulizer module 520 of similar diameter (e.g., between about 14 mm and about 20 mm) connects such that nebulized medicament is ejected along the longitudinal axis defined by a prong 510 for insertion into a nare of a patient. As gas is delivered into cannula 502 by gas supply tubes 506, the gas is directed in an axisymmetric radial manner by a flow director 518 positioned between prong 510 and nebulizer module 520. Nebulizer module 520 includes a housing 521 that couples the nebulizer module 520 to cylindrical body 504 of cannula 502. Flow director 518 includes anti-rotation baffles 530 that resist rotational flow but allow flow in the axial direction, for example, around flow director 518 before entering annular gap 519 formed between flow director 518 and nebulizer module 520. Baffles 530 are symmetrically arranged around flow director 518.

Nebulizer module 520 includes an emitter 508 embedded in a metal ring 522 having a piezo element 523, a printed circuit board 524 having spring pin contacts 526, wire leads 527 connected to printer circuit board 524, a first O-ring 528, and a second O-ring 529. First O-ring 528 seals the metal ring 522 against housing 521, and second O-ring 529 seals metal ring 522 against flow director 518. Spring pin contacts 526 allow a signal that is sent through wire leads 527 to be conducted to piezo element 523 (e.g., from a signal generator). Alternatively, wire leads 527 could be soldered directly to printed circuit board 524, or spring pin contacts 526 could be attached directly to wire leads 527 and positioned to contact piezo element 523. Emitter 508 is a vibrating mesh that is configured to vibrate at a frequency when an electric signal is applied to piezoelectric ring 522, such that medicament is nebulized and emitted from emitter 508 when in contact with the vibrating mesh of emitter 508. A reservoir 532 is formed in a cavity of housing 521 and provides medicament to emitter 508 for nebulization. The medicament in reservoir 532 is replenished via a fluid line 513. This configuration allows device 500 to self-recover, in that fluid is built up when device 500 is shut off, but the rate of nebulization and breathing gas flow rate will restart flow of medicament without needing to drain nebulizer module 520.

In FIG. 5, the breathing gas 514, shown with arrows, follows a flow path from gas supply tubes 506, past baffles 530, through annular gap 519, past emitter 508, and into prong 510. Nebulized particles 512 are shown as dots flowing from emitter 508 into prong 510 generally along the centerline of prong 510 as they are entrained in the flow of breathing gas 514. As discussed above in relation to FIGS. 3A-4B, flow director 518 is configured to direct breathing gas 514 from annular gap 519 in a radial axisymmetric manner towards emitter 508 positioned along the centerline of prong 510. Nebulized particles 512 are emitted into the axisymmetric flow so as to prevent particles 512 from being directed towards any walls of cannula 502. Due to this configuration, the nebulized particles 512 substantially follow the centerline of prong 510, and there are no direction changes to cause particles 512 to impinge against the internal walls of prong 510, reducing the likelihood of rain-out occurring during medicament delivery.

Nebulizer module 520 may be configured to be removably attached to flow director 518 or cylindrical body 504 of cannula 502. For example, housing 521 attaches to cannula 502 using a snap-fit connection, a magnetic connection, or a twist-lock connection. Flow director 518 may be shaped to have an interference fit with cylindrical body 504 inside prong 510 and around the inside of the cylindrical body 504. This configuration ensures a leak-free interface between the components when nebulizer module 520 is plugged into cannula 502. Flow director 518 may be configured to couple to the inlet of prong 510. O-rings 528 and 529 may be configured to enable liquid-tight seals, further ensuring a leak-free interface.

Rotational flow is to be avoided, as it causes particles 512 to be moved to the outside walls of the conduit by centrifugal force. To prevent this, anti-rotation baffles 530 that resist rotational flow but allow flow in the axial direction are employed around flow director 518. In some implementations, at least 1, 2, 3, 4, 5, or 6 baffles are positioned around flow director 518.

The medicament reservoir 532 is formed in housing 521 and fed by fluid line 513. Reservoir 532 may be sized small enough to reduce bulk on the cannula, maintaining patient comfort. Fluid line 513 may be formed by micro-bore tubing. In some implementations, a larger reservoir is contained within a capital unit having a fluid pump configured to pump the medicament to reservoir 532 via fluid line 513. In some implementations, medicament is fed through fluid line 513 by gravity, and the reservoir 532 is positioned above cannula 502 when in use. In some implementations, medicament is fed through fluid line 513 by a syringe pump. Medicament may be supplied to reservoir 532 continuously, intermittently, or upon user command via a controller. In some implementations, reservoir 532 can be refilled via an inlet in housing 521. A cap may be placed on the inlet to prevent spillage.

As shown in FIG. 5, fluid line 513 is contained within one of gas supply tubes 506, and wire leads 527 are contained within the other gas supply tube 506; however, alternative configurations are possible. Wire leads 527 and/or fluid line 513 may be routed inside one or both of gas supply tubes 506, are co-extruded with gas supply tubes 506 so as to be embedded inside the walls of the tubing (e.g., to form e-tubing), affixed externally to gas supply tubes 506 by spiraling around the tubing, adhesives, clips, or another attachment method, or are routed entirely separately from gas supply tubes 506. In some implementations, breathing gas 514 only enters cannula 520 from one of gas supply tubes 506 while the other contains only wire leads 527 and fluid line 513. In some implementations, cannula 502 includes a 3-to-1 valve for inlets of breathing gas 514, medicament, and electrical connection.

Wire leads 527 may be connected to a capital unit which supplies the breathing gas 514 to gas supply tubes 506 and/or contains a processor configured to control the function of nebulizer module 520. This may be particularly useful in feedback control of nebulization when certain physiological parameters are monitored during the administration of respiratory therapy and nebulized medicament. Such physiological parameters may include breathing patterns, inspiratory/expiratory ratio, oxygen level (e.g., blood oxygen saturation (SpO2) or fraction of inspired oxygen (FiO2)), carbon dioxide level, disease status, and disease stage. For example, the capital unit, a controller, or a processor may send instructions to nebulizer module 520 via wire leads 527 to increase, decrease, turn on, or turn off nebulization based one or more physiological parameters. In some implementations, medicament is nebulized intermittently in synchronization with patient breathing detected via breath sensing, such that medicament is only delivered during patient inspiration.

Suitable sources of pressurized breathing gas will be known to one of ordinary skill in the art. For example, the source may be the Vapotherm Flowrest System, Vapotherm Palladium System, Precision Flow unit, or the Vapotherm 2000i, all of which are provided by Vapotherm, Inc. of Exeter, New Hampshire, USA. For example, the source may be the respiratory therapy systems described in U.S. patent application Ser. No. 16/901,902 and U.S. patent application Ser. No. 15/783,566 (U.S. Publication No. 2018/0104436), each of which is incorporated herein by reference in its entirety. Other suitable sources of breathing gas will be known to one of ordinary skill in the art from the description herein.

The source of breathing gas 514 may be fluidically connected to gas supply tubes 506 via a delivery tube (not shown) comprising an inlet configured to receive breathing gas 514 from the source and a split outlet configured to divide and transmit breathing gas 514 into the flows of breathing gas 514 to each of gas supply tubes 506, respectively. Device 500 may be integrated in a respiratory therapy system having a breathing gas source and, optionally, a humidifying device (e.g., a vapor transfer unit or hotpot humidifier). Alternatively, device 500 may be implemented as an add-on unit configured to couple to any compatible respiratory therapy system with a breathing gas source and, optionally, a humidifying device (e.g., a vapor transfer unit or hotpot humidifier). Device 400 may be used with a system that provides heated and humidified breathing gas 514.

Suitable flowrates of breathing gas 514 range from about 1 L/min to about 80 L/min. In some implementations, the breathing gas flowrate and nasal prong inner diameter are chosen such that the exit velocity of breathing gas 514 from nasal prong 510 is at least about 40 m/s. In some implementations, the exit velocity is between about 40 m/s and about 75 m/s for a balance effective flushing of $CO_2$ from the patient airway and patient comfort or noise reduction. For example, prong 510 has an internal diameter of about 1.0 mm to about 4.0 mm.

Any of flow director 518, housing 521, and cannula 502 may be manufactured by injection molding a material such as plastic. Alternatively, cannula 502 may be manufactured by coating or dip molding one or more mandrels with a material such as plastic. Suitable materials for cannula 502, flow director 518, and housing 521 include a soft rubber, a rubber-like material, molded silicone, a thermoplastic elastomer (TPE), or dip molded polyvinyl chloride (PVC).

Figure 6:
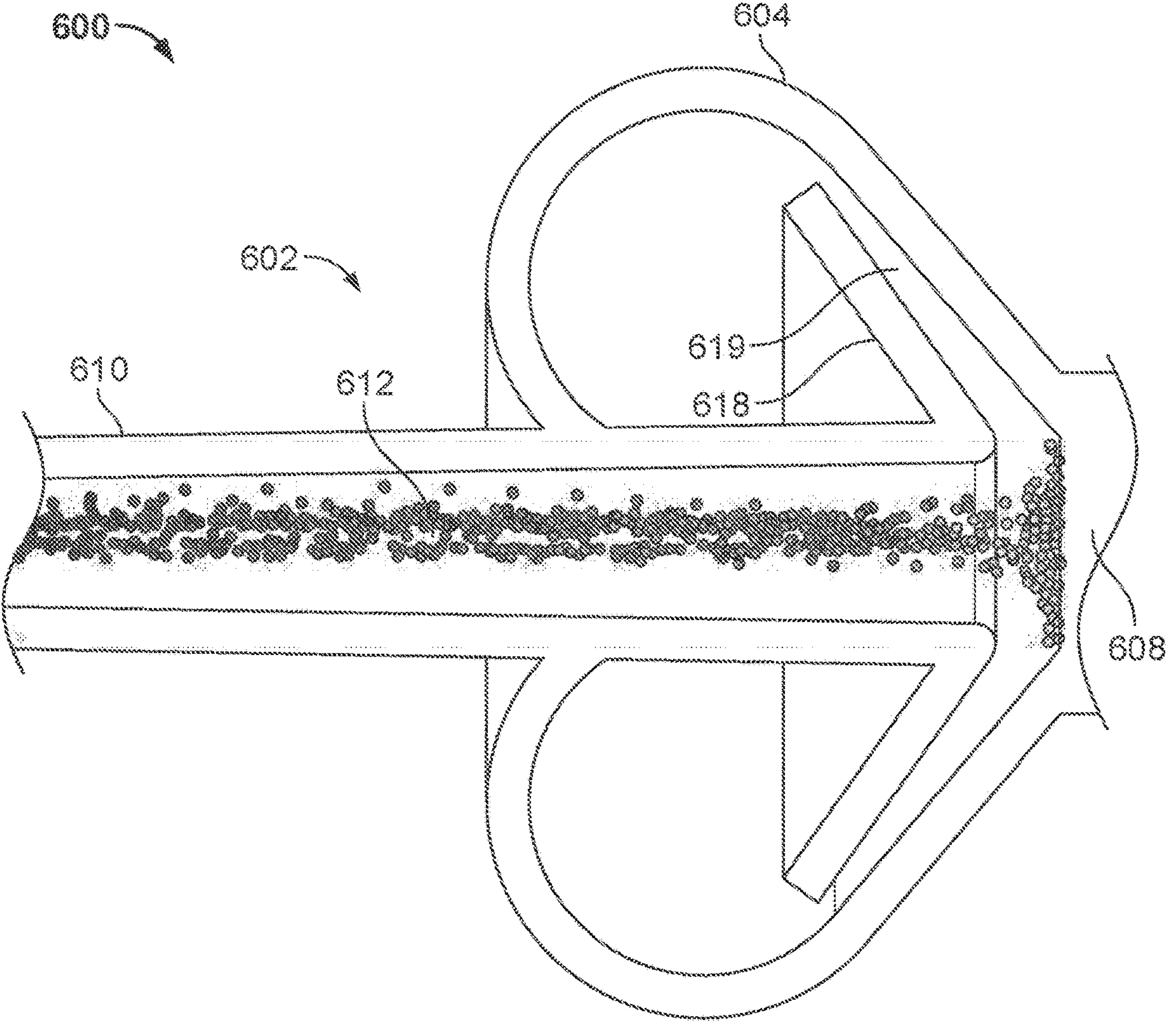
FIG. 6 shows a cross-section of a simulation of aerosolized particle flow in an internal mounted nebulizer cannula, according to an illustrative implementation.

FIG. 6 shows a cross-section of a portion of a device 600 including a cannula 602 having an emitter 608, a prong 610 for insertion into a nare of a patient, and a flow director 618 configured to form an annular gap 619 that enables axisymmetric radial flow of breathing gas to entrain nebulized medicament particles 612 to flow along a longitudinal axis of prong 610. The distribution of nebulized particles 612 in FIG. 6 represents the results of a computational fluid dynamics (CFD) simulation using a nebulized particle size of 5 microns with a gas flow rate of 20 L/min. Breathing gas flows from tube inlets (not shown), through annular gap 619, past emitter 608, and into prong 610. As discussed above in relation to FIGS. 3A-5, flow director 618 is configured to direct breathing gas from annular gap 619 in a radial axisymmetric manner towards emitter 508 positioned along the centerline of prong 610. Nebulized particles 612 are emitted into the axisymmetric flow so as to prevent particles from being directed towards any walls of cannula 602. High pressure drop from annular gap 619 and axisymmetric radial flow produces a highly concentrated and parallel flow of nebulized particles 619 entrained in breathing gas. Due to this configuration, the nebulized particles 612 substantially follow the centerline of prong 610, and there are no direction changes to cause particles to impinge against the internal walls of prong 610, reducing the likelihood of rain-out occurring during medicament delivery. Device 600 may be any of devices 300, 400, and 500 of FIGS. 3A/3B, 4A/4B, and 5, respectively.

Figure 7:
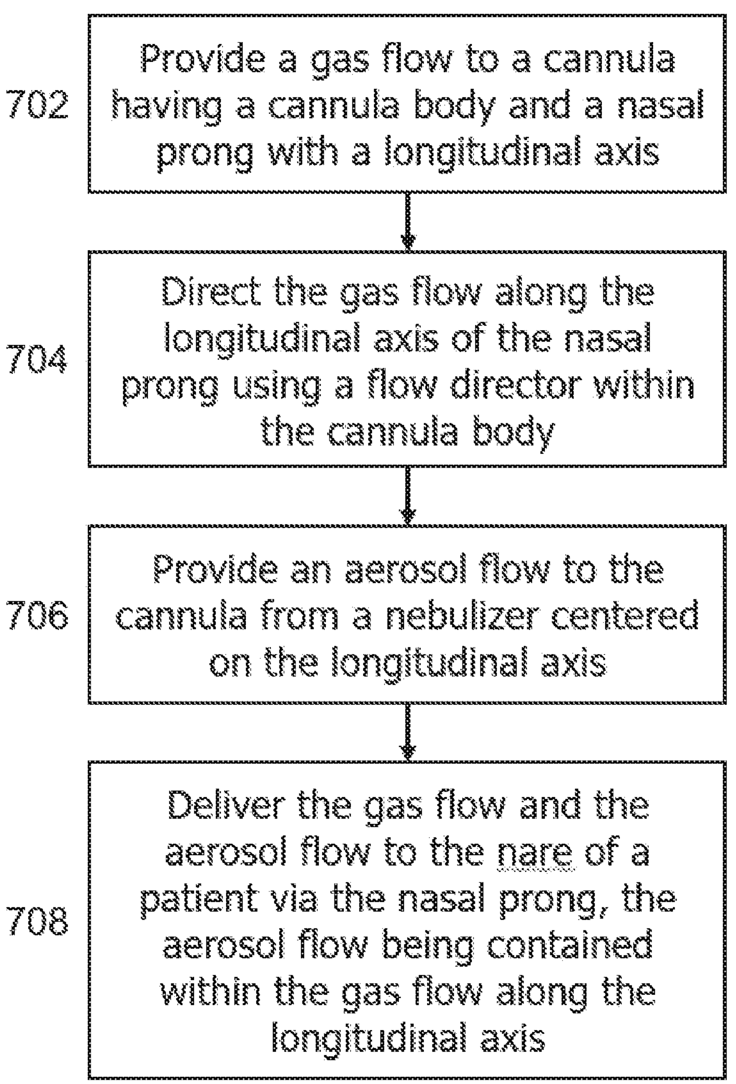
FIG. 7 shows a flowchart describing a method for providing respiratory therapy via an internal mounted nebulizer cannula, according to an illustrative implementation.

FIG. 7 shows a flowchart describing a method 700 for providing respiratory therapy to a patient. Method 700 comprises steps 702, 704, 706 and 708. Step 702 involves providing a flow of breathing gas to a cannula having a cannula body, first and second inlet tubes, and a nasal prong, such that the flow of breathing gas is supplied to the cannula body. The nasal prong has an inlet in fluid communication with the cannula body and an outlet for insertion into the nare of the patient. Step 704 involves directing the flow of breathing gas using a flow director contained within the cannula body such that the breathing gas flows along the longitudinal axis of the nasal prong. Step 706 involves providing a flow of aerosolized medicament to the cannula from a nebulizer having an aerosol generator positioned along and centered on the longitudinal axis, the aerosol generator configured to generate the flow of aerosolized medicament from a liquid medicament. Step 708 involves delivering the flow of breathing gas and the flow of aerosolized medicament to the nare of the patient via the nasal prong, the flow of aerosolized medicament being contained within the flow of breathing gas as it moves along the longitudinal axis of the nasal prong towards the nare of the patient. The cannula used in method 700 may be any of cannulas 302, 402, 502, or 602 described above in relation to FIGS. 3A/3B, 4A/4B, 5, and 6, respectively. As discussed above, the flow director of the cannula produces a radial axisymmetric flow of breathing gas out of an annular gap such that the aerosolized medicament becomes entrained in the flow of breathing as it flows into the nasal prong without any changes in direction, thus reducing the likelihood of rain-out.

In some implementations, the method further involves a step of directing the flow of breathing gas into the nasal prong along a path having a breathing gas axis that is symmetric along the longitudinal axis of the nasal prong. This step describes how the breathing gas is directed into the nasal prong in such a manner that aerosolized medicament emitted from the aerosol generator will flow into the breathing gas and into the nasal prong along the breathing gas axis to generate a generally parallel and concentrated flow of aerosol that is kept away from walls of the cannula.

In some implementations, the method further involves a step of forming an annular gap between an inlet of the nasal prong and the nebulizer. The annular gap is defined by the flow director's positioning relative to the other components. For example, the annular gap may be delimited by the flow director, which may be integrally formed with the nasal prong inlet, and a metal ring or housing of the nebulizer. The flow director may be configured such that the flow of breathing gas has a largest pressure drop in the nasal cannula across the annular gap. For example, the pressure drop in the flow of breathing gas across the annular gap is at least 30%. The flow of breathing gas may pass through the annular gap with the same velocity at any point along the annular gap, for example, equidistant from the longitudinal axis. This ensures that the flow will pass through all portions of the annular gap evenly, as any area with a tendency to have a higher flow rate would also have a higher pressure drop. This is shown in FIG. 3B depicting a cross-sectional view of device 300 along line B of FIG. 3A. The annular gap directs the flow of breathing gas axisymmetrically inwards towards the aerosol generator positioned along the longitudinal axis.

All of the flow vectors originating from the annular gap meet at the longitudinal axis, so there is a point with very low flow rate along or near the longitudinal axis. Theoretically, this point may have zero flow. The aerosol generator may be positioned near or at this point, and particles are never directed towards the walls of the cannula, because the flow is minimized and uniformly directed toward the longitudinal axis. In some implementations, the flow of breathing gas is axisymmetric about the longitudinal axis of the nasal prong up to the point of theoretical zero flow rate, after which the flow is axially orientated with respect to the longitudinal axis of the nasal prong. For example, the flow of breathing gas up to the point of theoretical zero flow rate is radial, substantially radial or directed towards the longitudinal axis, or forms a shape that is any one of conical, hyperbolic, parabolic, and circular. The flow director may have a funnel shape to facilitate directing the gas along the longitudinal axis. The nasal prong may have a hyperbolic or parabolic cross-section to further encourage axisymmetric flow via gradual acceleration of the flow.

In some implementations, the method further involves a step of preventing rotation of the flow of breathing gas from the first and second inlet tubes via an anti-rotation element.

For example, the anti-rotation element comprises a plurality of baffles symmetrically arranged about the flow director. Rotational flow is to be avoided, as it causes particles to be moved to the outside walls of the conduit by centrifugal force. To prevent this, the anti-rotation element that resists rotational flow but allows flow in the axial direction can be employed around the flow director. In some implementations, at least 1, 2, 3, 4, 5, or 6 baffles are positioned around the flow director. The orientation of the first and second inlet tubes can also be arranged so that the inlet tubes point toward the longitudinal axis of the nasal prong instead of being offset from it. If two equal-flow inlets are used, they can be positioned symmetrically opposite another about the longitudinal axis to cancel these effects, thus preventing rotational flow.

In some implementations, the method further involves a step of providing an electric signal to the aerosol generator of the nebulizer via a wire to enable aerosolization of the liquid medicament. As discussed above in relation to FIGS. 4B and 5, wire leads may be provided to send signals to the aerosol generator, which may comprise a piezoelectric element and vibrating mesh that function by vibrating at a frequency that produces aerosol particles from liquid medicament when the electric signal is provided (e.g., continuously or intermittently). The wire may be connected to an external device such as a capital unit or nebulizer controller that allows for operation of the nebulizer based on feedback control and/or user commands.

In some implementations, the method further involves a step of supplying the liquid medicament to the nebulizer from a supply bag via a feed line comprising micro-bore tubing. The supply bag may be configured to hang from a hook, for example, on a rolling cart, in order to supply the liquid medicament by gravity. The supply bag may alternatively be a reservoir contained in a capital unit. An electric pump or syringe pump may be used to convey the liquid medicament from the supply bag via the feed-line. In other implementations, the nebulizer comprises a reservoir that has an inlet and cap for refilling the reservoir.

The first and second inlet tubes may also be connected to a capital unit or other source of breathing gas via a delivery tube. Suitable sources of pressurized breathing gas will be known to one of ordinary skill in the art. For example, the source may be the Vapotherm Flowrest System, Vapotherm Palladium System, Precision Flow unit, or the Vapotherm 2000i, all of which are provided by Vapotherm, Inc. of Exeter, New Hampshire, USA. For example, the source may be the respiratory therapy systems described in U.S. patent application Ser. No. 16/901,902 and U.S. patent application Ser. No. 15/783,566 (U.S. Publication No. 2018/0104436), each of which is incorporated herein by reference in its entirety. Other suitable sources of breathing gas will be known to one of ordinary skill in the art from the description herein. The source of breathing gas may be fluidically connected to the inlet tubes via a delivery tube comprising an inlet configured to receive breathing gas from the source and a split outlet configured to divide and transmit breathing gas into the flows of breathing gas to each of first and second inlet tubes, respectively. The cannula may be integrated in a respiratory therapy system having a breathing gas source and, optionally, a humidifying device (e.g., a vapor transfer unit or hotpot humidifier). Alternatively, the cannula may be implemented as an add-on unit configured to couple to any compatible respiratory therapy system with a breathing gas source and, optionally, a humidifying device (e.g., a vapor transfer unit or hotpot humidifier). The cannula may be used with a system that provides heated and humidified breathing gas.

Figure 8:
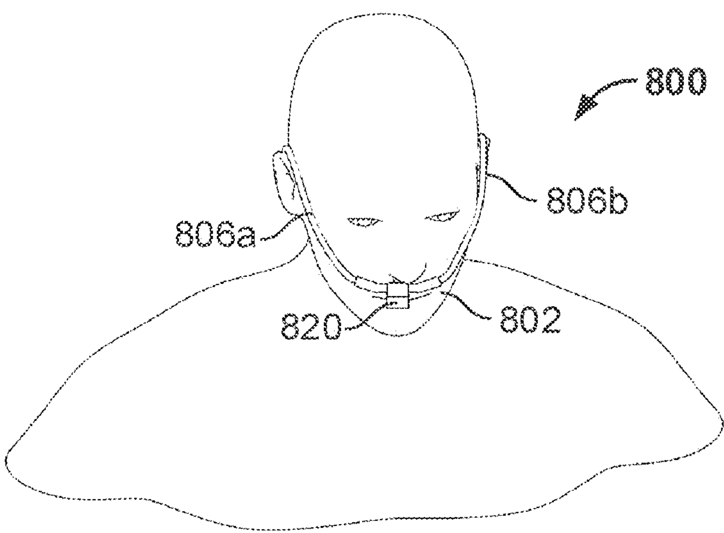
FIG. 8 shows a patient equipped with a nasal cannula with internally mounted nebulizer, according to an illustrative implementation.

FIG. 8 shows a patient equipped with a device 800 including a cannula 802, a nebulizer 820, and gas supply tubes 806*a* and 806*b*. Device 800 may be any of the devices described in relation to FIGS. 3A-7. Gas supply tubes 806*a* and 806*b* supply breathing gas to cannula 802. Cannula 802 includes a prong inserted in a nare of the patient for delivery of the breathing gas with nebulized medicament. Nebulizer 820 is mounted on cannula 802 to emit a flow of nebulized medicament into the flow of breathing gas directly before the gas is delivered into the nare.

An emitter of nebulizer 820 may be aligned with the prong in order to produce a parallel flow of gas and nebulized medicament for delivery with minimized rain-out and higher entrainment efficiency. A flow director according to the above description may be employed to generate an axisymmetric flow of the gas at the point where nebulized medicament is introduced into the gas. Any of the flow directors described in relation to FIGS. 3A-7 may be used.

In this illustrated implementation of FIG. 8, gas supply tubes 806*a* and 806*b* are configured as lariat tubes that loop around the cars of the patient, such that tubes 806*a* and 806*b* rest atop the cars for stability of device 800. Tubes 806*a* and 806*b* may be reinforced to prevent kinking of the tubes as they curve around the cars. Suitable mechanisms of reinforcement include a braid, one or more parallel struts, one or more perpendicular struts, and a spiral structure. The reinforcements may be disposed on, around, or within the tubes 806*a* and 806*b* or may be co-extruded with the tubes during manufacture. While the tubes 806*a* and 806*b* are configured as lariat tubes in FIG. 8, it is to be understood that other mechanisms may be employed for stabilizing device 800 such as a stabilizing brace, a head gear, a clip, or an adhesive. In some implementations, only one of tubes 806*a* and 806*b* supplies gas to cannula 802, while the other contains a fluid feed line and/or electrical wires for supplying nebulizer 820 with medicament and controlling the operation of nebulizer 820, respectively.

While the cannulas described herein generally have one nasal prong, it should be understood that any of the cannulas in relation to FIGS. 2A-8 can be configured to have two nasal prongs configured for insertion into the nares of a patient. For example, breathing gas is delivered from gas supply tubes into the cannula, and the breathing gas containing nebulized medicament is directed into both of the two nasal prongs. This dual prong configuration is particularly advantageous as it allows a user, operator, or controller to manage which prong is delivering medicament and/or breathing gas, for example, if one of the patient's nares is blocked/occluded. Each nasal prong may have an internal diameter of about 1.0 mm to about 4.0 mm, and the flow rate through a dual prong cannula may be between 1 L/min to about 60 L/min.

In some implementations, the cannula includes two flow directors (such as the flow directors described in relation to FIGS. 3A-7), such that each flow director generates a radial axisymmetric flow of breathing gas into one of the nasal prongs. In some implementations, two emitters are employed, with each emitter being positioned along a longitudinal axis of one of the nasal prongs. Both emitters may be in fluid communication with a single drug reservoir, or each emitter is fluidically connected to a distinct drug reservoir. The cannula may include a dividing wall to keep a first cannula portion fluidically separate from a second cannula portion, where the first cannula portion includes a first gas supply tube, a first flow director, and a first emitter, and the second cannula portion includes a second gas supply tube, a second flow director, and a second emitter. In some implementations, the first cannula portion and the second cannula portion are separated by a bridge (e.g., a hollow bridge not in fluid communication with both of the first and second cannula portions). In some implementations, the bridge contains a drug reservoir in fluid communication with one or both of the first and second emitters. The first emitter and second emitter may be operatively coupled to a controller configured to control operation of both emitters. For example, the controller can turn on, turn off, and adjust flow rates of each of the first and second emitters to decide which nare of the patient receives nebulized medicament.

The configurations described herein should be understood to be applicable to types of patient adaptors other than nasal cannulas and to types of respiratory therapy other than high flow nasal therapy. In some implementations, any of the cannulas described in relation to FIGS. 3A-6 may be used for mechanical ventilation, CPAP, BiPAP, or low flow oxygen therapy. For example, a patient interface configured for mechanical ventilation may have a flow director for creating an axisymmetric flow of breathing gas from gases supplied to the patient interface and for directing the axisymmetric flow into an outlet of the patient interface, such that the flow is axisymmetric about and substantially parallel to a longitudinal axis defined by the outlet of the patient interface. The patient adapter also includes a nebulizer positioned along the longitudinal axis defined by the outlet of the patient interface such that nebulized medicament particles are emitted from the nebulizer in a direction parallel with the flow of breathing gas along the longitudinal axis and into the outlet of the patient interface. The breathing gas exits the outlet with the nebulized medicament particles entrained in its flow and is delivered to the patient. In some implementations, the patient interface is a mask configured to deliver the flow of breathing gas and nebulized medicament into the mouth of a patient. In some implementations, the patient interface is a tracheostomy tube configured to deliver the flow of breathing gas and nebulized medicament directly into a patient's airway (trachea). For use with mechanical ventilation, the patient interface may have shape and size adjusted (relative to that of the cannulas in FIGS. 3A-6) according to those of skill in the art to account for differences in ventilation rate, anatomy of the administered location of the patient interface, type of medicament administered, breathing gas composition, or inclusion of additional devices on the patient interface such as breath sensing technology.

The foregoing is merely illustrative of the principles of the disclosure, and the apparatuses can be practiced by other than the described implementations, which are presented for purposes of illustration and not of limitation. It is to be understood that the apparatuses disclosed herein, while shown for use in high flow therapy systems, may be applied to systems to be used in other ventilation circuits.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

The invention claimed is:

1. A system for delivery of breathing gas and aerosolized medicament to a patient, the system comprising:

a delivery tube configured to supply a flow of breathing gas;

a nebulizer configured to supply a flow of nebulized medicament; and a nasal interface having a first inlet, a second inlet, a mixing chamber in fluid communication with the first inlet and the second inlet, and an outlet in fluid communication with the mixing chamber to deliver a mixed flow of breathing gas and nebulized medicament, wherein the first inlet is coupled to a distal end of the delivery tube to receive the flow of breathing gas into the mixing chamber, and wherein the second inlet is coupled to an emitter of the nebulizer to receive the flow of nebulized medicament directly into the mixing chamber, the nasal interface further comprising a flow director having a first portion and a second portion;

wherein the mixing chamber and the second inlet are aligned with a longitudinal axis of the outlet, such that mixing of the flow of breathing gas and the flow of nebulized medicament occurs directly behind the outlet and along a direction coaxial with the longitudinal axis, the second inlet positioned along the longitudinal axis at a point at which the flow of breathing gas has a theoretical zero flow rate, and wherein the first portion of the flow director is coupled to the nasal interface and adapted to receive the flow of breathing gas from the first inlet and direct the flow of breathing gas into the mixing chamber such that the breathing gas flows along the longitudinal axis, and the second portion is secured to the nebulizer and configured such that the flow of nebulized medicament is contained within the flow of breathing gas as it moves along the longitudinal axis of the outlet for delivery to the patient.

2. The system of claim 1, wherein the outlet is a nasal prong.

3. The system of claim 2, wherein the nasal prong has a hyperbolic or parabolic cross section.

4. The system of claim 1, wherein the breathing gas flows into the outlet along a path having a breathing gas axis that is symmetric along the longitudinal axis.

5. The system of claim 1, wherein the flow director forms an annular gap along a breathing gas flow path between the first inlet and the mixing chamber.

6. The system of claim 5, wherein the flow director is configured such that the flow of breathing gas has a pressure drop in the nasal interface that is largest across the annular gap.

7. The system of claim 6, wherein the pressure drop in the flow of breathing gas across the annular gap is at least 30%.

8. The system of claim 5, wherein the flow of breathing gas passes through the annular gap with a flow velocity that is constant at any point along the annular gap.

9. The system of claim 1, wherein the flow of breathing gas is axisymmetric about the longitudinal axis of the nasal prong up to the point of theoretical zero flow rate, after which the flow is axially orientated with respect to the longitudinal axis.

10. The system of claim 9, wherein the flow of breathing gas about the longitudinal axis up to the point of theoretical zero flow rate is radial, substantially radial or directed towards the longitudinal axis.

11. The system of claim 9, wherein the flow of breathing gas about the longitudinal axis of the nasal prong up to the point of theoretical zero flow rate forms a shape that is any one of conical, hyperbolic, parabolic and circular.

12. The system of claim 1, wherein the flow director further comprises an anti-rotation element which prevents rotation of the flow of breathing gas within the nasal interface as it is supplied via the first inlet.

13. The system of claim 12, wherein the anti-rotation element comprises a plurality of baffles symmetrically arranged about the flow director.

14. The system of claim 1, wherein the nebulizer is removably attached to the nasal interface.

15. The system of claim 1, wherein the emitter of the nebulizer comprises a vibrating mesh.

16. The system of claim 15, wherein the vibrating mesh is attached to a piezoelectric element.

17. The system of claim 16, wherein the piezoelectric element is in electrical contact with a controller on a printed circuit board.

18. The system of claim 17, wherein the piezoelectric element is in electrical contact with the printed circuit board via spring contact pins.

19. The system of claim 18, further comprising wires that are in electrical contact with the printed circuit board for transmitting electrical signals from a signal generator to the vibrating mesh.

20. The system of claim 19, wherein the wires are threaded through the delivery tube.

21. The system of claim 20, further comprising a housing that is attached to the nasal interface.

22. The system of claim 21, wherein the housing comprises injection molded plastic.

23. The system of claim 21, wherein the housing is attached to the nasal interface using a snap-fit connection.

24. The system of claim 21, wherein the housing contains a reservoir filled with liquid medicament, the reservoir arranged such that the liquid medicament is in contact with an inner surface of the vibrating mesh.

25. The system of claim 24, wherein the housing contains O-rings to achieve a liquid tight seal between the vibrating mesh and the housing.

26. The system of claim 24, wherein the flow of aerosolized medicament is emitted from an outer surface of the emitter.

27. The system of claim 24, wherein the reservoir is in fluid communication with a liquid feed line.

28. The system of claim 27, wherein the liquid feed line is threaded through the delivery tube.

29. The system of claim 28, wherein the liquid feed line comprises micro-bore tubing.

30. The system of claim 1, wherein the delivery tube is in fluidic communication with a source of breathing gas.

31. The system of claim 1, wherein the nasal interface comprises a soft rubber, a rubber-like material, molded silicone, a thermoplastic elastomer (TPE), or dip molded polyvinyl chloride (PVC).

32. The system of claim 1, wherein the medicament comprises at least one of: bronchodilators, surfactants and antibiotics.

33. The system of claim 1, wherein the liquid medicament comprises at least one of: Albuterol (Ventolin), Salbutamol (Proventil), Levosalbutamol/Levalbuterol (Xopenex), Curosurf (Chiesi Pharmaceuticals), Alveofact (Boehringer Ingelheim), Survanta (Abbott Laboratories), Exosurf (Glaxo Wellcome), Surfaxin (Discovery Laboratories), macrolides, erythromycin, clarithromycin, azithromycin, glycopeptides, vancomycin, teicoplanin, oxazoldinone, quinupristin/dalfopristen, aminoglycosides, gentamicin, tobramycin, amikacin, streptomycin, netilmicin, quinolones, ciprofloxacin, ofloxacin, levofloxacin, tetracyclines, oxytetracycline, doxycycline, minocycline, cotrimoxazole, colistin, imepinim, meripenim, pumactant, lucinactant, poractant alfa, beractant, calfactant, Beraksurf, Venticute, and colfosceril palmitate.

* * * * *